US009012139B2

(12) United States Patent
Collard et al.

(10) Patent No.: US 9,012,139 B2
(45) Date of Patent: Apr. 21, 2015

(54) TREATMENT OF DYSTROPHIN FAMILY RELATED DISEASES BY INHIBITION OF NATURAL ANTISENSE TRANSCRIPT TO DMD FAMILY

(75) Inventors: Joseph Collard, Delray Beach, FL (US); Olga Khorkova Sherman, Tequesta, FL (US)

(73) Assignee: CuRNA, Inc., Miami, FL (US)

( * ) Notice: Subject to any disclaimer, the term of this patent is extended or adjusted under 35 U.S.C. 154(b) by 0 days.

(21) Appl. No.: 13/318,734

(22) PCT Filed: May 7, 2010

(86) PCT No.: PCT/US2010/034026
§ 371 (c)(1),
(2), (4) Date: Nov. 3, 2011

(87) PCT Pub. No.: WO2010/129861
PCT Pub. Date: Nov. 11, 2010

(65) Prior Publication Data
US 2012/0046345 A1  Feb. 23, 2012

Related U.S. Application Data

(60) Provisional application No. 61/176,594, filed on May 8, 2009, provisional application No. 61/317,350, filed on Mar. 25, 2010.

(51) Int. Cl.
| C12Q 1/68 | (2006.01) |
| C12N 15/85 | (2006.01) |
| C07H 21/02 | (2006.01) |
| C07H 21/04 | (2006.01) |
| A61K 31/713 | (2006.01) |
| C12N 15/113 | (2010.01) |

(52) U.S. Cl.
CPC ............ *A61K 31/713* (2013.01); *C12N 15/113* (2013.01); *C12N 2310/11* (2013.01); *C12N 2310/113* (2013.01); *Y10T 436/143333* (2015.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |
| 6,100,090 A | 8/2000 | Monia et al. |
| 6,140,492 A | 10/2000 | Morelli et al. |
| 6,147,200 A | 11/2000 | Manoharan et al. |

(Continued)

FOREIGN PATENT DOCUMENTS

| CA | 2686933 | 4/2008 |
| EP | 335451 A2 | 10/1989 |

(Continued)

OTHER PUBLICATIONS

Lu et al. (PNAS, 2005, vol. 102, No. 1, pp. 198-203).*
Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34(1993).
Boutla, A., et al., "Short 5'-phosphorylated double-stranded RNAs induce RNA interference in Drosophila," Curr. Biol, 11:1776-1780 (2001).

(Continued)

*Primary Examiner* — Amy Bowman
(74) *Attorney, Agent, or Firm* — CuRNA, Inc.; Monte R. Browder

(57) ABSTRACT

The present invention relates to antisense oligonucleotides that modulate the expression of and/or function of Dystrophin family, in particular, by targeting natural antisense polynucleotides of Dystrophin family. The invention also relates to the identification of these antisense oligonucleotides and their use in treating diseases and disorders associated with the expression of DMD family.

11 Claims, 8 Drawing Sheets

(56) References Cited

U.S. PATENT DOCUMENTS

| | | |
|---|---|---|
| 6,165,712 A | 12/2000 | Foulkes et al. |
| 6,165,990 A | 12/2000 | Singh et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Wengel et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tanguay et al. |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,320,965 B2 | 1/2008 | Sah et al. |
| 7,321,828 B2 | 1/2008 | Cowsert et al. |
| 7,314,923 B2 | 2/2008 | Kaneko et al. |
| 7,335,764 B2 | 2/2008 | Crooke et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 2003/0139359 A1 | 7/2003 | Dobie |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner |
| 2007/0213274 A1 | 9/2007 | Salonen |
| 2007/0213292 A1 | 9/2007 | Stoffel et al. |
| 2007/0248590 A1 | 10/2007 | Milne et al. |
| 2008/0146788 A1 | 6/2008 | Bhat et al. |
| 2008/0221051 A1 | 9/2008 | Becker et al. |
| 2008/0293142 A1 | 11/2008 | Liu et al. |
| 2009/0191263 A1 | 7/2009 | Reich et al. |
| 2009/0192106 A1 | 7/2009 | Dobie et al. |
| 2009/0208479 A1 | 8/2009 | Jaye et al. |

(56) References Cited

U.S. PATENT DOCUMENTS

| | | |
|---|---|---|
| 2009/0258925 A1 | 10/2009 | Wahlestedt |
| 2009/0318536 A1 | 12/2009 | Freier et al. |
| 2009/0326041 A1 | 12/2009 | Bhanot et al. |
| 2010/0105760 A1 | 4/2010 | Collard et al. |

FOREIGN PATENT DOCUMENTS

| | | | |
|---|---|---|---|
| EP | 335451 A3 | 3/1998 | |
| WO | WO-84/03564 | 9/1984 | |
| WO | WO-91/19735 | 12/1991 | |
| WO | WO-92/00091 | 1/1992 | |
| WO | WO-92/08796 | 5/1992 | |
| WO | WO-93/20242 | 10/1993 | |
| WO | WO-94-26887 A1 | 11/1994 | |
| WO | WO-94/28143 | 12/1994 | |
| WO | WO-95-15373 A2 | 6/1995 | |
| WO | WO-95/22618 | 8/1995 | |
| WO | WO-95/25116 | 10/1995 | |
| WO | WO-95/35505 | 12/1995 | |
| WO | WO-96-27663 A2 | 9/1996 | |
| WO | WO-97-39120 A1 | 10/1997 | |
| WO | WO-99-14226 A1 | 3/1999 | |
| WO | WO-99-39352 A1 | 8/1999 | |
| WO | WO-00-57837 A1 | 10/2000 | |
| WO | WO-00-61770 A2 | 10/2000 | |
| WO | WO-01-00669 A2 | 1/2001 | |
| WO | WO-01-21631 A2 | 3/2001 | |
| WO | WO-01-25488 A2 | 4/2001 | |
| WO | WO-01-51630 A1 | 7/2001 | |
| WO | WO-02-062840 A1 | 8/2002 | |
| WO | WO-02-068688 A1 | 9/2002 | |
| WO | WO-2004-016255 A1 | 2/2004 | |
| WO | WO-2004-024079 A2 | 3/2004 | |
| WO | WO-2004-030750 A1 | 4/2004 | |
| WO | WO-2004-041838 A1 | 5/2004 | |
| WO | WO 2004/083446 A2 * | 9/2004 | ............ 514/44 |
| WO | WO-2004-104161 A2 | 12/2004 | |
| WO | WO-2005-045034 A2 | 5/2005 | |
| WO | WO-2005-070136 A2 | 8/2005 | |
| WO | WO-2005-079862 A1 | 9/2005 | |
| WO | WO-2007-028065 A2 | 3/2007 | |
| WO | WO-2007-071182 A2 | 6/2007 | |
| WO | WO-2007-087113 A2 | 8/2007 | |
| WO | WO-2007-138023 A1 | 12/2007 | |
| WO | WO-2008-057556 A2 | 5/2008 | |
| WO | WO-2008-066672 A2 | 6/2008 | |
| WO | WO-2008-087561 A2 | 7/2008 | |
| WO | WO-2010-002984 A1 | 1/2010 | |
| WO | WO-2010-040571 A2 | 4/2010 | |
| WO | WO-2010-054364 A1 | 5/2010 | |
| WO | WO-2010-058227 A2 | 5/2010 | |

OTHER PUBLICATIONS

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biolotry vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Flourescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N.J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al, "Gene expression profiling: monitoring transcription and translation products using DNA microarrays and proteomics," FEBS Lett., 480;2-16 (2000).

Chabala, J.C., "Solid-phase combinatorial chemistry and novel tagging methods for identifying leads," Curr Opin Biotechnol, 6:632-639 (1995).

Cech, J., "Ribozymes and Their Medical Implications,"American. Med Assoc. 260:3030-3035 (1988).

Chen, et al., "Expression of ssDNA in Mammalian Cells." BioTechniques 34:167-171 (2003).

Chen, et al., "Analogous Organic Synthesis of Small-Compound Libraries: Validation of Combinatorial Chemistry in Small-Molecule Synthesis," J. Amer. Chem. Soc. 116:2661-2662 (1994).

Cheng, J. et al., "Transcriptional maps of 10 human chromosomes at 5-nucleotide resolution," Science 308:5725:1149-1154 (2005).

Cho, et al., "An Unnatural Biopolymer," Science 261:1303-1305 (1993).

Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).

Cubitt, et al., "Understanding, improving and using green flourescent proteins," Trends in Biochemical Science 20:448-455 (1995).

Curiel, D. T. et al., "Adenovirus enhancement of transferrin-polylysine-mediated gene delivery," PNAS 88:8850-8854 (1991).

Dai et al., "SIRT1 Interacts with p73 and Suppresses p73-Dependent Transcriptional Activity," J Cell Physiol 210(1):161-165 (2007).

Davidson, et al., "A model system for in vivo gene transfer into the central nervous system using an adenoviral vector," Nat. Genet 3:219-223 (1993).

Davis, et al., "Direct Gene Transfer into Skeletal Muscle In Vivo: Factors Affecting Efficiency of Transfer and Stability of Expression," Hum Gene Ther 4:151-159 (1993).

De Mesmaeker, et al., "Antisense Oligonucleotides," Acc. Chem. Res. 28:366-374 (1995).

Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).

Dixon, et al., "Anthrax," New England J. Med. 341:815-826 (1999).

Dolle, "Discovery of Enzyme inhibitors through combinatorial chemistry," Mol Divers. 2:223-236 (1997).

Eguchi, et al., "Antisense RNA," Annu. Rev. Biochem 60:631-652 (1991).

Eichler, et al., "Generation and utilization of synthetic combinatorial libraries," Mol Med Today 1:174-180 (1995).

Eichler, et al., "Peptide Peptidomimetic and organic synthetic combinatorial libraries," Med Res Rev 15:481-496 (1995).

Espeseth, et al., "A genome wide analysis of ubiquitin ligases in APP processing identifies a novel regulator of BACE1 mRNA levels," Mol. Cell Neurosci. 33: 227-235 (2006).

Faghihi, M. & Wahlestedt, C., "RNA interference is not involved in natural antisense mediated regulation of gene expression in mammals," Genome Biol (2005).

Fauchere, et al., "Peptide and nonpeptide lead discovery using robotically synthesized soluble libraries," Can J. Physiol Pharmacol 75:683-689 (1997).

Felgner and Holm, "Cationic Liposome-Mediated Transfection," Bethesda Res. Lab Focus, 11:2:21 (1989).

Fields, et al., "How many genes in the human genome?" Nature Genetics 7:345-346 (1994).

Freier & Altman, "The ups and downs of nucleic acid duplex stability: structure-stability studies on chemically-modified DNA:RNA duplexes," Nucl. Acid Res., 25:22:4429-4443 (1997).

Fuchs, et al., "Identification of Differentially Expressed Genes by Mutually Subtracted RNA Fingerprinting,"Anal. Biochem., 286:91-98 (2000).

(56) References Cited

OTHER PUBLICATIONS

Gebeyehu, G., et al., "Novel biotinylated nucleotide-analogs for labeling and colorimetric detection of DNA," Nucl. Acids Res. 15:4513 (1987).
Geller, A.I. et al., "An HSV-1 Vector Expressing Tyrosine Hydroxylase Causes Production and Release of L-DOPA front Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I. et al., "Infection of cultured central nervous system neurons with a defective herpes simplex virus 1 vector results in stable expression of *Escherichia coli* β-galactosidase," PNAS USA 87:1149-1153 (1990).
Giuliano, et al., "Fluorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-3904 (1999).
Hagihara, et al., "Vinylogaus Polypeptides: An Alternate Peptide Backbone," J. Amer, Chem, Soc, 114:6568-6571 (1992).
Heller, et al., "Discovery and analysis or inflammatory disease-related genes using cDNA Microarrays," PNAS U.S.A. 94:2150-2155 (1997).
Herdewijn P., "Hetercyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et at., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome," Nature 431:7011:931-945 (2004).
Janda, K.D. "Tagged versus utagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Micorbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997(2005).
Katayama, S. et al., "Antisense Transcription in the Mammalian Transcriptome," Science 309:1564-1566 (2005).
Kawahara & Nishikura., "Extensive adenosine-to-inosine editing detected in Alu repeats of antisense RNAs reveals scarcity of sense-antisense duplex formation," FEBS Lett 580;2301-2305 (2006).

Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, 1980 pp. 75-77.
Larson et al., "Rapid DNA Fingerprinting of Pathogens by Flow Cytometry," Cytometry, 2000, 41:203-208 (2000).
Larsson, et al., "High-throughput protein expression of cDNA products as a tool in functional genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleolides: Synthesis, properties, and activity as inhibitors of replication of human immunodeficiency virus in cell culture," PNAS 86:6553-6356 (1989).
Li et al., "Control of APP processing and Aβ generation level by BACE1 enzymatic activity and transcription," Faseb J 20; 285-292 (2006).
Li, et al., J. Neurochem 89 1308-1312 (2004a).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg, Med. Chem. Let 4;1053 (1994).
Manoharan, et al., "Oligonucieotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-171 (1989).
Morelli et al., "The antisense *bcl-2-IgH* transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol, Chem., vol. 280, No. 40, pp. 34025-334032 (2005).

(56) References Cited

OTHER PUBLICATIONS

Prasanth, et al., "Regulating Gene Expression through RNA Nuclear Retention," Cell 123, 249-263 (2005).

Prashar & Weissman, "READS: A Method for Display of 3'-End Fragments of Restriction Enzyme-Digested cDNAs for Analysis of Differential Gene Expression," Methods Enzymol., 303:258-272 (1999).

Quantin, et al., "Adenovirus as an expression vector in muscle cells in vivo," PNAS 89:2581-2584(1992).

Rosenfeld, et al., "In Vivo Transfer of the Human Cystic Fibrosis Transmembrane Conductance Regulator Gene to the Airway Epithelium," Cell, 68:143-155 (1992).

Rosok and Sioud, "Systematic identification of sense-antisense transcripts in mammalian cells," Nature Biotech. 22(1):104-108 (2004).

Saison-Behmoaras, et al., "Short modified antisense oligonucteolides directed against Ha-ras point mutation induce selective cleavage of the mRNA and inhibit T24 cells proliferation," EMBO J. 10:1111-1118 (1991).

Sanghvi, Y.S., in Crooke, S.T. and Lebleu, B., eds., Antisense Research and Applications, CRC Press, Boca Raton, 1993, p. 276-278

Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).

Schena, et al., "Parallel human genome analysis: Microarray-based expression monitoring of 1000 genes," PNAS 93:10614-10619(1996).

Shea, et al., "Synthesis, hybridization properties and antiviral activity of lipid-oligodeoxynucleotide conjugates," Nucl. Acids Res 18:3777-3783 (1990).

Shimomura, et al., "Semi-synthetic aequorin," J. of Biochemistry (Tokyo) 251:405-410 (1988).

Singer, et al., "Targeting BACE1 with siRNAs ameliorates Alzheimer disease neuropathology in a transgenic model," Nat Neurosci 8:1343-1349 (2005).

Southwick, et al., "Cyanine Dye Labeling Reagents—Carboxymethylindocyanine Succinimidyl Esters," Cytometry 11:418-430 (1990).

Stratford-Perricadet, et al., "Widespread Long-term Gene Transfer to Mouse Skeletal Muscles and Heart," J. Clin. Invest., 90:626-630 (1992).

Sullenger, et al., "Overexpression of TAR sequences Renders Cells Resistant to Human Immunodeficiency Virus Replication," Cell63:601-608 (1990).

Sun et al., "Downregulation of Sirt1 by antisense oligonucleotides induces apoptosis and enhances radiations sensitization in A549 lung cancer cells," Lung Cancer 58(1):21-29 (2007).

Sutcliffe, et al., "TOGA: An automated parsing technology for analyzing expression of nearly all genes," PNAS, 97:1976-1981(2000).

Sutton, et al., "TIGR Assembler: A New Tool for Assembling Large Shotgun Sequencing Projects," Genome Science & Tech., 1:9-19 (1995)

Svinarchuk, et al., "Inhibition of HIV proliferation in MT-4 cells by antisense oligonucleotide conjugated to lipophilic groups," Biochimie 75:49-54 (1993).

Tamagno, et al., "The various aggregation states of β-amyloid 1-42 mediate different effects on oxidative stress, neurodegeneration, and BACE-1 expression," Free Radic Biol. Med. 41:202-212 (2006).

Thakker, D.R., et al., "siRNA-mediated knockdown of the serotonin transporter in the adult mouse brain," Mol Psychiatry 10:782-789 (2005).

Thakker, et al., "Neurochemical and behavioral consequences of widespread gene knockdown in the adult mouse brain by using nonviral RNA interference," PNAS 101:17270-17275 (2004).

Thomas et al., "Intracellular pH Measurements in Ehrlich Ascites Tumor Cells Utilizing Spectroscopic Probes Generated in Situ," Biochemistry 18:2210-2218 (1979).

Thompson, et al., "Synthesis and Applications of Small Molecule Libraries" Chem Rev 96:555-600 (1996).

To, KY, "Identification of Differential Gene Expressionm by High Throughput Analysis," Comb. Chem. High Throughput Screen 3:235-241 (2000).

Tong, et al., "Oxidative stress potentiates BACE1 gene expression," Neural Transm 112, 455-469 (2005).

Toulme, J.J., "New candidates for true antisense," Nature Biotechnology 19:17-18 (2001).

Tsien in Methods in Cell Biology vol. 30 Taylor and Wang (eds) p. 127-156 (1989).

Ulhman, E., "Recent advances in the medical chemistry of antisense oligonucleotide," Current Opinions in Drug Discovery & Development 3:203-213 (2000).

Van Den Eynde BJ, "T cell defined tumor antigens," Curr Opin Immunol 9:684-693 (1997).

Van Der Bruggen, et al., "Tumor-specific shared antigenic peptides recognized by human T cells," Immunol Rev188:51-64 (2002).

Vanhee-Brossolet and Vaquero, "Do natural antisense transcripts make sense in eukaryotes?" Gene 211:1-9 (1998).

Vaughn, et al., "Human Antibodies with Sub-nanomolar Affinities Isolated from a Large Non-immunized Phage Display Library," Nature Biotechnology, 14:3:309-314 (1996).

Velculescu, et al., "Serial Analysis of Gene Expression," Science 270;484-487 (1995).

Wahlestedt, "Natural antisense and noncoding RNA transcripts as potential drug targets," Drug Discovery Today 11 (11/12):503-508 (2006).

Wahlestedt, C., "Antisense oligonucleotide strategies in neuropharmacology," Trends Pharmacol Sci 15:2:42-46 (1994).

Walsh, et al., "The role of cell-derived oligomers of Aβ in Alzheimer's disease and avenues for therapeutic intervention," Biochem Soc Trans 33: 1087-1090 (2005).

Wang, B.B. et al., "Identification of a nuclear-specific cyclophilin which interacts with the proteinase inhibitor eglin c," Biochem J. 314 (Pt 1) 313-319 (1996).

Wiesenhofer et al., "Glial cell line-derived neurotrophic factor (GDNP) is a proliferation factor for rat C6 glioma cells: evidence from antisense experiments," Antisense & Nucleic Acid Drug Development 10(5):311-321 (2000).

Xue, et al., "Hypoxia and reoxygenation increased BACE1 mRNA and protein levels in human neuroblastoma SH-SY5Y cells," Neurosci Lett 405,231-235 (2006).

Yang, et al., "Cellular and Humoral Immune Responses to Viral Antigens Create Barriers to Lung-Directed Gene Therapy with Recombinant Adenoviruses," J. Virol 69:2004-2015 (1995).

EP Application No. 06850393.7 Examination Report dated Oct. 18, 2011.

International Search Report and Written Opinion for PCT Application No. PCT/US2010/033078 mailed Jun. 29, 2011.

PCT/US2010/026119 Search Report and Written Opinion mailed Feb. 7, 2011.

PCT/US2010/024079 Search Report and Written Opinion mailed Jan. 31, 2011.

PCT/US2010/027394 Search Report and Written Opinion mailed Nov. 5, 2010.

Bernstein, E. et al., "Role for a Bidentate Ribonuclease in the Initiation Step of RNA Interference," Nature 409:363-366, (2001).

Yamada et al., "Endothelial Nitric-Oxide Synthase Antisense (NOS3AS) Gene Encodes an Autophagy-Related Protein (APG9-like2) Highly Expressed in Trophblast": The Journal of Biological Chemistry, vol. 280, No. 18: 18283-18290, (2005).

PCT/US96/10287 (WO97/000271) The Regents of the University of California dated Jan. 3, 1997.

International Search Report corresponding to PCT/US2010/034026 dated Mar. 24, 2011.

* cited by examiner (SEQ ID NO: 1)

Natural antisense sequence (BF838561): SEQ ID NO: 3

[sequence text illegible]

Natural antisense sequence (BG208074): SEQ ID NO: 4

[sequence text illegible]

Natural antisense sequence (BF960643): SEQ ID NO: 5

[sequence text illegible]

Natural antisense sequence (BF768753): SEQ ID NO: 6

[sequence text illegible]

Natural antisense sequence (ENST00000431309): SEQ ID NO: 7

[sequence text illegible]

FIG.4

| Sequence ID | Antisense Sequence Name | Sequence |
|---|---|---|
| SEQ ID NO:8 | CUR-0636 | [sequence illegible] |
| SEQ ID NO:9 | CUR-0638 | [sequence illegible] |
| SEQ ID NO:10 | CUR-0640 | [sequence illegible] |
| SEQ ID NO:11 | CUR-0642 | [sequence illegible] |
| SEQ ID NO:12 | CUR-0644 | [sequence illegible] |
| SEQ ID NO:13 | CUR-0646 | [sequence illegible] |
| SEQ ID NO:14 | CUR-0648 | [sequence illegible] |
| SEQ ID NO:15 | CUR-0650 | [sequence illegible] |
| SEQ ID NO:16 | CUR-0652 | [sequence illegible] |
| SEQ ID NO:17 | CUR-0654 | [sequence illegible] |

FIG.5

| Sequence ID | Antisense Sequence Name | Sequence |
|---|---|---|
| SEQ ID NO:18 | CUR-1443 | G*C*C*A*C*C*T*G*C*T*A*G*C*T*C*T*G*T*G*A |
| SEQ ID NO:19 | CUR-1444 | T*A*C*C*T*T*C*T*T*C*C*T*C*A*T*C*A*C*T |
| SEQ ID NO:20 | CUR-1445 | G*G*G*A*T*T*A*C*A*G*G*T*A*T*G*A*G*C*C*A*C |
| SEQ ID NO:21 | CUR-1446 | C*C*T*T*C*A*G*A*C*A*G*T*A*T*C*A*G*G*T*G*C |
| SEQ ID NO:22 | CUR-1447 | T*C*C*C*A*T*A*A*C*A*G*A*C*C*T*T*C*T*C*C*C |

FIG.6

| Sequence ID | Sense Sequence Name | Sequence |
|---|---|---|
| SEQ ID NO:23 | CUR-0636 | rCrUrCrArCrArGrArGrCrUrArGrCrArGrGrUrGrAGA |
| SEQ ID NO:24 | CUR-0638 | rCrUrGrArGrArAGrGrUrGrArUrGrArGrGrArArGCT |
| SEQ ID NO:25 | CUR-0640 | rGrCrUrCrAUrArCrCrUrGrUrArArUrCrCCT |
| SEQ ID NO:26 | CUR-0642 | rCrArUrArUrArGrCrCrArCrArArArUrArArArGrCrUrUC |
| SEQ ID NO:27 | CUR-0644 | rArGrArUrArArGrCrUrUrCrCrArGrUrUrGrGrCrGrGrA |
| SEQ ID NO:28 | CUR-0646 | rCrCrUrArArArCrGrUrCrArUrArUrGrArGrUrGrAA |
| SEQ ID NO:29 | CUR-0648 | rArGrGrArArGrArGrArGrUrArUrArUrCrArGrGrArUrCCU |
| SEQ ID NO:30 | CUR-0650 | rCrUrGrUrArGrUrCrUrGrArUrGrArArArGrUrCrACG |
| SEQ ID NO:31 | CUR-0652 | rGrUrGrUrArUrArGrArUrCrGrArUrArGrArArGrUrUAC |
| SEQ ID NO:32 | CUR-0654 | rCrCrGrUrCrArArCrUrCrCrUrArCrCrCrArUrUrCCT |

TREATMENT OF DYSTROPHIN FAMILY RELATED DISEASES BY INHIBITION OF NATURAL ANTISENSE TRANSCRIPT TO DMD FAMILY

FIELD OF THE INVENTION

The present application claims the priority of U.S. provisional patent application No. 61/176,594 filed May 8, 2009 and U.S. provisional patent application No. 61/317,350 filed Mar. 25, 2010 both of which are incorporated herein by reference in its entirety.

Embodiments of the invention comprise oligonucleotides modulating expression and/or function of DMD family and associated molecules.

BACKGROUND

DNA-RNA and RNA-RNA hybridization are important to many aspects of nucleic add function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drag, VITRAVENE™ (for treatment of cytomegalovirus retinitis), reflecting that antisense has therapeutic utility.

SUMMARY

This Summary is provided to present a summary of the invention to briefly indicate the nature and substance of the invention. It is submitted with the understanding that it will not be used to interpret or limit the scope or meaning of the claims.

In one embodiment, the invention provides methods for inhibiting the action of a natural antisense transcript by using antisense oligonucleotide(s) targeted to any region, of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of an DMD family polynucleotide in patient ceils or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 378 of SEQ ID NO: 3, 1 to 294 of SEQ ID NO: 4, 1 to 686 of SEQ ID NO: 5, 1 to 480 of SEQ ID NO: 6 and 1 to 501 of SEQ ID NO: 7 (FIG. 3) thereby modulating function and/or expression of the DMD family polynucleotide in patient cells or tissues in vivo or in vitro.

In another preferred embodiment, an oligonucleotide targets a natural antisense sequence of DMD family polynucleotides, for example, nucleotides set forth in SEQ ID NO: 3 to 7, and any variants, alleles, homologs, mutants, derivatives, fragments and complementary sequences thereto. Examples of antisense oligonucleotides are set forth as SEQ ID NOS: 8 to 22 (FIGS. 4 and 5).

Another embodiment provides a method of modulating function and/or expression of an DMD family polynucleotide in patient ceils or tissues in vivo or in vitro comprising contacting said cells or tissues with an antisense oligonucleotide 5 to 30 nucleotides in length wherein said oligonucleotide has at least 50% sequence identity to a reverse complement of the an antisense of the DMD family polynucleotide; thereby modulating function and/or expression of the DMD family polynucleotide in patient cells or tissues in vivo or in vitro.

Another embodiment provides a method of modulating function and/or expression of an DMD family polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to an DMD family antisense polynucleotide; thereby modulating function and/or expression of the DMD family polynucleotide in patient cells or tissues in vivo or in vitro.

In a preferred embodiment, a composition comprises one or more antisense oligonucleotides which bind to sense and/or antisense DMD family polynucleotides.

In another preferred embodiment, the oligonucleotides comprise one or more modified or substituted nucleotides.

In another preferred embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another preferred embodiment, the oligonucleotides are administered to a patient subcutaneously, intramuscularly, intravenously or intraperitoneally.

In another preferred embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another preferred embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 1:

Figure 1A:
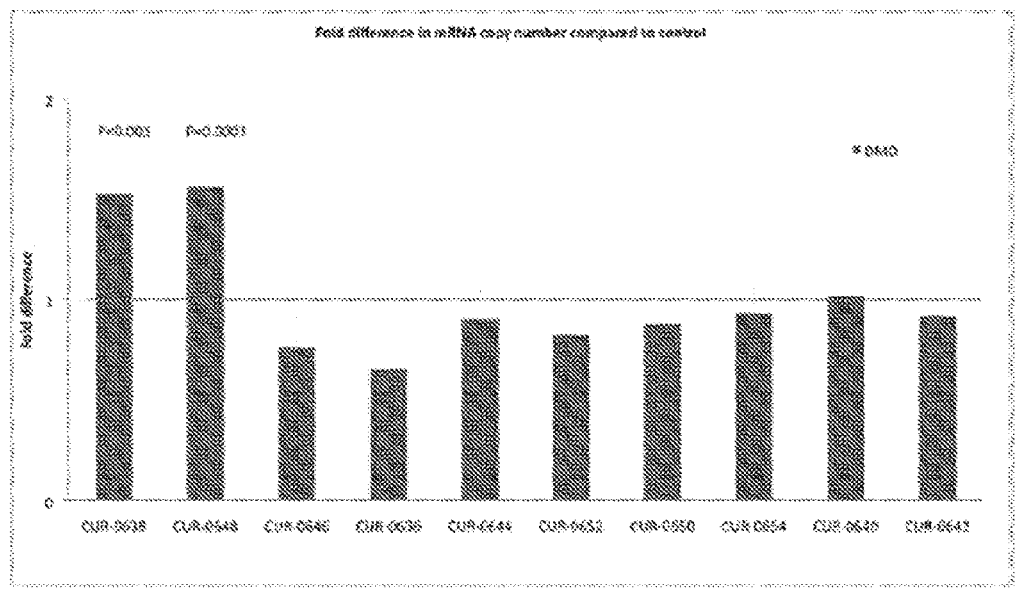
FIG. 1A is a graph of real time PCR results showing the fold change+standard deviation in DMD family mRNA after treatment of 518A2 cells with phosphorothioate oligonucleotides introduced using Lipofectamine 2000, as compared to control. Real time PCR results show that the levels of DMD family mRNA in 518A2 cells are significantly increased 48 h after treatment with two of the siRNAs designed to DMD family antisense BG208074. Bars denoted as CUR-0636 to CUR-0654, correspond to samples treated with SEQ ID NOS: 8 to 17 respectively.
Figure 1B:
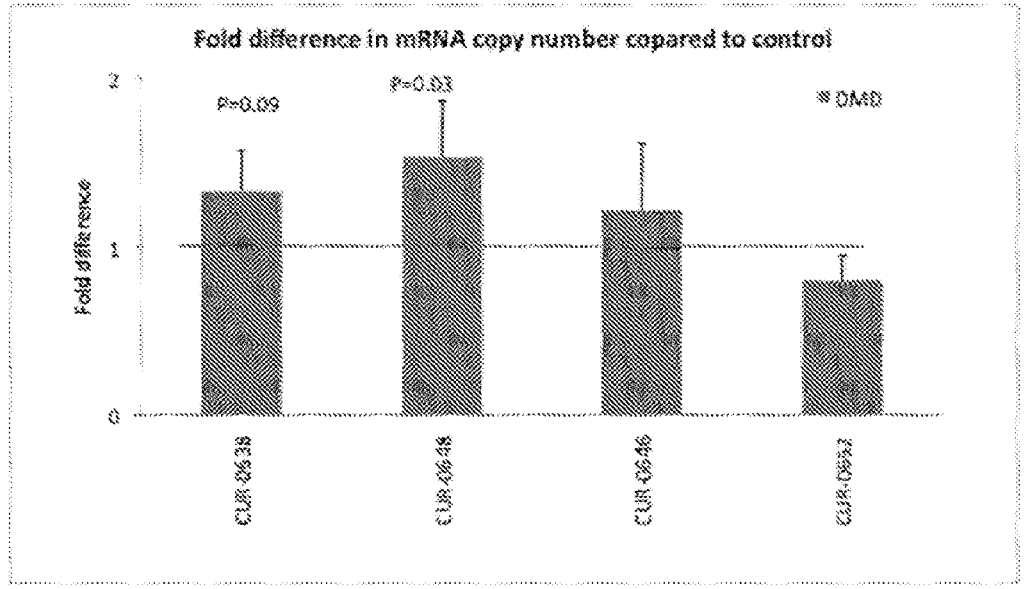
FIG. 1B is a graph of real time PCR results showing the fold change+standard deviation in DMD family mRNA after treatment of 518A2 ceils with phosphorothioate oligonucleotides introduced using Lipofectamine 2000, as compared to control. Treatment with siRNAs to other antisense molecules, BF83856L BF768753 and BF950643, did not elevate DMD family mRNA levels. Bars denoted as CUR-0638, CUR-0648, CUR-0646 and CUR-0652 correspond to samples treated with SEQ ID NOS: 9, 14, 13 and 16 respectively.

SEQ ID NO: 1: *Homo sapiens* Dystrophin family, transcript variant Dp427m, mRNA (NCBI Accession No.: NM_004006).

SEQ ID NO: 2: *Homo sapiens* Utrophin (UTRN), mRNA (NCBI Accession No.: NM_007124)

FIG. 3 shows

SEQ ID NO: 3: Natural DMD family antisense sequence (BF838561)

SEQ ID NO: 4: Natural DMD family antisense sequence (BG208074)

SEQ ID NO: 5: Natural DMD family antisense sequence (BF950643)

SEQ ID NO: 6: Natural DMD family antisense sequence (BF768753)

SEQ ID NO: 7: Natural UTRN antisense sequence (ENST00000431309),

FIG. 4 shows DMD antisense oligonucleotides, SEQ ID NOs: 8 to 17. 'r' indicates RNA.

FIG. 5 shows the UTRN antisense oligonucleotides, SEQ ID NOs: 18 to 22, * indicates phosphothioate bond.

FIG. shows the DMD sense oligonucleotides, SEQ ID NOs: 23 to 32. The sense oligonucleotides SEQ ID NO: 23 to 32 are the reverse complements of the antisense oligonucleotides SEQ ID NO: 8 to 17 respectively. 'r' indicates RNA.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context, in which it appears clearly indicates. Thus, for example, for the genes disclosed herein, which in some embodiments relate to mammalian nucleic acid and amino acid sequences are intended to encompass homologous and/or orthobgous genes and gene products from other animals including, but not limited to other mammals, fish, amphibians, reptiles, and birds. In preferred embodiments, the genes or nucleic acid sequences are human.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described, in the application and claims, unless otherwise stated the term "about" meaning within an acceptable error range for the particular value should be assumed.

As used herein, the term "aaRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) *Ann. Rev. Biochem.* 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oiigomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oiigomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anmeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "DMD family", "Dystrophin family" and "dystrophin-related protein family", "dystrophin gene family" are inclusive of all family members, mutants, alleles, fragments, species, coding and noncoding sequences, sense and antisense polynucleotide strands, etc.

As used herein, the words Dystrophin, DMD, BMD, CMD3B, DXS142, DXS164, DXS206, DXS230, DXS239, DXS268, DXS269, DXS270 and DXS272 are used interchangeably in the present application.

As used herein, the words Utrophin, UTRN, DMDL, DRP, DRP1, Dystrophin-related protein 1, FLJ23678,are used interchangeably in the present application.

As used herein, the words "dystrophin related protein 2", "dystrophin-related protein 2" and DRP2 are used interchangeably in the present application.

As used herein, the words Dystrobrevin α-dystrobrevin, β-dystrobrevin, DTNA and DTNB are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences (Caplen, N. J., et al. (2001) *Proc. Natl. Acad Sci.* USA 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) *Nature* 409:363-366). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) *Nature* 409:363-366; Boutla, A., et al. (2001) *Curr. Biol.* 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity (Cech, (1988) *J. American. Med. Assoc.* 260, 3030-3035). Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al. (1990) *Cell, 63*, 601-608). This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphornates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminepurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-florouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2-deoxy and 2'-hydroxy sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.,* 25(22), 4429-4443, Toulmé, J. J. (2001) *Nature* Biotechnology 19:17-18; Manoharan M., (1999) *Biochemica et Biophysica Acta* 1489:117-139; Freier S. M., (1997) *Nucleic Acid Research,* 25:4429-4443, Uhlman, E., (2000) *Drug Discovery &Development* 3: 203-213, Herdewin P., (2000) *Antisense & Nucleic Acid Drug Dev.,* 10:297-310); 2'-O, 3'-C-linked [3.2.0] bicycloarabionucleosides (see e.g. N. K. Christiensen, et al. (1998) *J. Am. Chem. Soc.,* 120: 5458-5463; Prakash T P, Bhat B. (2007) *Curr Top Med Chem.* 7(7):641-9; Cho E J, et al. (2009) *Annual Review of Analytical Chemistry,* 2, 241-264). Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizabfe" when binding of the compound to the target nucleic acid interferes with the normal junction of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the ease of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oiigomeric compounds hybridize to a target sequence are determined by the nature and composition of the oiigomeric compounds and the assays in which they arc being investigated. In general, stringent hybridization conditions comprise low concentrations (<0.15M) of salts with inorganic cations such as Na++ or K++ (i.e., low ionic strength), temperature higher than 20° C.-25° C. below the Tm of the oiigomeric compound:target sequence complex, and the presence of denaturants such as formamide, dimethylfomiamidc, dimethyl sulfoxide, or the detergent sodium dodecyi sulfate (SDS). For example, the hybridization rate decreases 1.1% for each 1% formamide. An example of a high stringency hybridization condition is 0.1×X sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between, the oligonucleotide and the target nucleic acid is considered to be a complementary position. The oligomeric compound and the further DNA, RNA, or oligonucleotide molecule are complementary to each other when a sufficient number of complementary positions in each molecule are occupied fay nucleotides which can hydrogen bond with each other. Thus, "specifically liybridizabie" and "complementary" are terms which are used to indicate a sufficient degree of precise pairing or complementarity over a sufficient number of nucleotides such that stable and specific binding occurs between the oiigomeric compound and a target nucleic acid.

It is understood in the art that the sequence of an oiigomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oiigomeric compounds of the present invention comprise at least about 70%, or at least about 75%, or at least about 80%, or at least about 85%, or at least about 90%, or at least about 95%, or at least about 99% sequence complementarity to a target region, within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., (1990) *J. Mol. Biol.,* 215,403-410; Zhang and Madden, (1997) *Genome Res.,* 7,649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic add concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pB 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, aeylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc).

As used, herein, "cancer" refers to ail types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to; fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian: cancer lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

As used herein, a "muscle disease or disorder" includes but is not limited to muscular dystrophy (MD), a muscle-wasting disease, inflammatory myopathy or myositis (including, for example, dermatomyositis, polymyositis, inclusion body myotosis), myotubular myopathy, nemaline myopathy, a desmin related myopathy, Marfan myopathy, a mitochondrial myopathy etc. As used herein, muscular dystrophy refers to a group of genetic, hereditary muscle diseases that cause progressive muscle weakness and which may be characterized by progressive skeletal muscle weakness, defects in muscle proteins, and the death of muscle cells and tissue. Muscular dystrophy includes, but is not limited to Duchenne (DMD family), Becker (BMD), Spinal Muscular Atrophy, Spinal bulbar muscular atrophy, dystrophinopathy, sarcoglycanopathy, limb girdle muscular dystrophy (LGMD), congenital muscular dystrophy (CMD), facioscapulohumeral (FSHD), myotonic, oculopharyngeal, distal, and Emery-Dreifuss.

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinating diseases, spinal cord disorders, and disorders of peripheral, nerves, muscle and neuromuscular junctions. Addiction and mental, illness, include, but are not limited to, bipolar disorder and schizophrenia, are also included, in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral, sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myeiinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIVassociated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsam disease; infantile spasms; inflammatory myopathy; intracranial cyst; intracranial hypertension; Joubert syndrome; Kearns-Sayre syndrome; Kennedy disease Kinsboume syndrome; Klippel Fell syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease: Lennox-Gustaut syndrome; Leseh-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly: migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupos; neuromyotonia; neuronal ceroid lipofuscinosis; neuronal migration disorders; Niemann-Pick disease; O'Sulivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Virus dance; Sandhoff disease; Schilder's disease; schizencephaly; septa-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multt-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome. As used herein, a "neuromuscular disease or disorder" refers to any disease adversely affecting both nervous elements (brain, spinal cord, peripheral nerve) and muscle (striated or smooth muscle), including but not limited to involuntary movement disorders, dystonias, spinal cord injury or disease, multiple sclerosis, myasthenia gravis, Parkinson's disease. Amyotrophic Lateral Sclerosis (ALS), Huntington's disease, Lambert-Eaton Myasthenic Syndrome (LES), Congenital Myasthenic Syndromes (CMS), Charcot-Marie-Tooth Disease (CMT), Dejerine-Sottas Disease (DS), Creutzfeldt-Jakob disease, Friedreich's Ataxia, muscular dystrophy, spasticity from cerebral palsy and stroke.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to DMD family activation, CVS diseases include, hut are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

As used herein, "cardiomyopathy" refers to any disease or dysfunction of the myocardium (heart muscle) in which the heart Is abnormally enlarged, thickened and/or stiffened. As a result, the heart muscle's ability to pump blood is usually weakened. The disease or disorder can be, for example, inflammatory, metabolic, toxic, infiltrative, fibroplastic, hematological, genetic, or unknown in origin. Such cardiomyopathies may result from a lack of oxygen. Other diseases include those that result from myocardial injury which involves damage to the muscle or the myocardium in the wall of the heart as a result of disease or trauma. Myocardial injury can be attributed to many things such as, but not limited to, cardiomyopathy, myocardial infarction, or congenital heart disease. Specific cardiac disorders to be treated also include congestive heart failure, ventricular or atrial septal defect, congenital heart defect or ventricular aneurysm. The cardiac disorder may be pediatric in origin. Cardiomyopathy includes but is not limited to, cardiomyopathy (dilated, hypertrophic, restrictive, arrhythmogenic and unclassified cardiomyopathy), sporadic dilated cardiomyopathy, X-linked Dilated Cardiomyopathy (XLDC), acute and chronic heart failure, right heart failure, left heart, failure, biventricular heart failure, congenital heart defects, mitral valve stenosis, mitral valve insufficiency, aortic valve stenosis, aortic valve insufficiency, tricuspidal valve stenosis, tricuspidal valve insufficiency, pulmonal valve stenosis, pulmonal valve insufficiency, combined valve defects, myocarditis, acute myocarditis, chronic myocarditis, viral myocarditis, diastolic heart failure, systolic heart failure, diabetic heart failure and accumulation diseases.

Polynucleotide and Oligonucleotide Compositions and Molecules

Targets: In one embodiment, the targets comprise nucleic acid sequences of Dystrophin family, including without limitation sense and/or antisense noncoding and/or coding sequences associated with DMD family.

Dystrophin has been known since 1987, (Hoffman et al. (1987), Cell. 51:509-517) to be the protein that is deficient in Duchenne muscular dystrophy (DMD). This is an elongated protein present at the cytoplasmic surface of the vertebrate muscle cell membrane (Hoffman et al. (1987), Cell. 51:509-517). Three other dystrophin-related proteins, i.e., $DRP_1$ (dystrophin-related protein Type 1, or utrophin), $DRP_2$ (dystrophin-related protein Type 2), and dystrobrevins, have also been identified as products of different genes (Wang et al. (1998) Hum Mol Genet. 7:581-588). Dystrophins and atrophia have been detected in muscle of other mammalian species (Pons et al. (1994) Circulation, 90:369-374; Wang et al. (1998) Hum Mol Genet. 7:581-588; Rafael et al. (2000) Hum Mol Genet. 9:1357-1367) and also in other tissues, such as the electric organ, that are derived from skeletal muscle (Chang et al. (1989) J Biol Chem. 264:20831 -20834), and in nerves (Rivier et al. (1999a) Histochem J. 31:425-432, Rivier et al. (1999b) J Muscle Res Cell Moul. 20:305-314) of T. marmorata. Dystrophin in mammal skeletal muscle interacts with an associated protein complex (DAPC) to form a link between the cytoskeleton and the extracellular matrix (Ibraghimov-Beskrovnaya et al. (1992) Nature, 355:696-702). This complex consists of two dystroglycans (α-and β-) (Deys et al. (1995) J Biol Chem. 270:25956-25959), sarcoglycans (α-, βd-, γ-, δ-, and c) that are complexed with sarcospan (Nigro et al. (1996) Hum Mol Genet. 5:1179-1186; Crosbie et al. (1997) J Biol Chem. 272:31221-31224; McNally et al. (1998) FEBS Lett. 422:27-32), and three syntrophins (α-, β1-, β2-) in muscle tissues (Ahn et al. (1996) J Biol Chem 271:2724-2-730). However, new isoforms of syntrophins (γ1- and γ2-) have also been reported and were found expressed as brain-specific protein (Piluso et al. (2000) *J Biol Chem.* 275; 15851-15860), Deficiency or variations in some associated proteins generate a different muscle pathology, but the pathogenesis of all of these related muscular dystrophies is still unclear. This may be due to the heterogeneity of the data recorded, e.g., clue to the existence of four dystrophin-related proteins that all share homology with dystrophin's cysieine-rich and C-terminal domains and also because of the muscle type analyzed.

Dystrophin is a rod-shaped cytoplasmic protein, and a vital part of a protein complex that connects the cytoskeleton of a muscle fiber to the surrounding extracellular matrix through the cell membrane. This complex is variously known as the costamere or the dystrophin-associated protein complex. Many muscle proteins, such as a dystrobrevin, syncoilin, synemin, sarcoglycan, dystroglycan, and sarcospan, colocalize with dystrophin at the costamere.

Its deficiency is one of the root causes of muscular dystrophy. Normal tissue contains small amounts of dystrophin (about 0.002% of total muscle protein), but its absence leads to both DMD family and fibrosis, a condition of muscle hardening. A different mutation of the same gene causes defective dystrophin, leading to Becker's muscular dystrophy (BMD). Thus, it would be of great therapeutic value to modulate the expression and/or function of dystrophin in cells, tissues or organs of patients in need of such treatment.

Dystrophin family, the largest known human gene, encodes a protein called dystrophin. There are many different versions of dystrophin, some of which are specific to certain ceil types. Dystrophin is located chiefly in muscles used for movement (skeletal muscles) and the muscles of the heart (cardiac muscles). Small amounts of the protein are present in nerve cells in the brain.

In skeletal and cardiac muscles, dystrophin is part of a protein complex that strengthens muscle fibers and. protects them from injury as muscles contract and relax. The dystrophin complex acts as an anchor, connecting each muscle cell's structural framework (cytoskeleton) with the lattice of proteins and other molecules outside the cell. The dystrophin complex may also play a role in cell signaling by interacting with proteins that send and receive chemical, signals.

Little is known about the function of dystrophin in nerve cells and without wishing to be bound by theory, dystrophin could be important for the normal structure and function of synapses.

Duchenne and Becker muscular dystrophy are caused by mutations in the DMD family gene.

Muscular dystrophy (MD) refers to a group of genetic disorders whose major symptom is muscle wasting. There are two major forms of MD, differing in severity and age of onset. In Duchenne muscular dystrophy, symptoms are noticeable in early childhood and quickly become debilitating. Becker muscular dystrophy, on the other hand, is of later onset and less severe. Both forms of MD are caused by mutations in the dystrophin gene, a large (2.6 Mb) gene comprised of 97 exons. The dystrophin protein plays an important structural role as part of a large complex in muscle fiber membranes. When dystrophin is missing or non-functional, the entire complex is compromised, leading to degeneration of muscle tissue. When the ability to regenerate the muscle is exhausted, muscle wasting occurs.

Mutations in the DMD family gene also cause a form of heart disease called X-linked dilated cardiomyopathy. This condition enlarges and weakens the cardiac muscle, preventing it from pumping blood efficiently. Although dilated cardiomyopathy is a sign of Duehenne and Becker muscular dystrophy, the isolated X-linked form of this heart condition is not associated with weakness and wasting of skeletal muscles.

Utrophin is a 395 kDa protein encoded by multiexonic 1 Mb UTRN gene located on chromosome 6q24 (Pearce, et al. (1993) *Hum Mol Gene.* 2: 1765 1772). The structure of the gene bears large similarities to that of the dystrophin gene, in contrast to dystrophin, the utrophin gene has a long 5' untranslated region, split over two exons, and it is proceeded by an HTF-island. In mouse, the gene maps to chromosome 10. Utrophin is distributed throughout the sarcolemma in fetal and regenerating muscle, but is down-regulated in normal adult muscle and is restricted to the myotendinous and neuromuscular junctions (Blake et al., 1996). In the dystrophin deficient mdx mouse, utrophin levels in muscle remain elevated soon after birth compared with normal mice; once the utrophin levels have decreased to the adult levels (about 1 week after birth) the first signs of muscle fibre necrosis are detected. However, there is evidence to suggest that in the small calibre muscles, continual increased levels of utrophin can interact with the DGC complex (or an antigenicaliy related complex) at the sarcolemma thus preventing loss of the complex with the result that these muscles appear normal. There is also a substantial body of evidence demonstrating that utrophin is capable of localising to the sarcolemma in normal muscle. During fetal muscle development there is increased utrophin expression, localised to the sarcolemma, up until 18 weeks in the human and 20 days gestation in the mouse. After this time the utrophin sarcolemma staining steadily decreases to the significantly lower adult levels shortly before birth where utrophin is localised almost exclusively to the NMJ. The decrease in utrophin expression coincides with increased expression of dystrophin. See reviews (Ibraghimov Beskrovnaya, et al. (1992) *Nature* 355, 696 702, Blake, et al. (1994) Trends in Cell Biol, 4: 19 23, Tinsley, et al. (1993) *Curr Opino Genet Dev.* 3:484 90).

DRP2 is predicted to resemble certain short C-terminal isoforms of dystrophin and dystrophin-related protein 1 (DRP1 or utrophin). DRP2 is a relatively small protein, encoded in man by a 45 kb gene localized to Xq22. It is expressed principally in the brain and spinal cord, and is similar in overall structure to the Dp116 dystrophin isoform.

Dystrobrevin, a member of the dystrophin family of proteins, was originally identified from the *Torpedo californica* electric organ as an 87-kDa phosphoprotein associated with the cytoplasmic face of the postsynaptic membrane (Wagner K R. et al. (1993) *Neuron.* 10:531-522; Carr C, et al. (1989) *J Cell Biol.* 109:1753-1764). It has been postulated that the 87-kDa protein plays a role in synapse formation or stability because it copurifles with acetylcholine receptors from the electric organ membranes. In mammalian, skeletal muscle, dystrophin is found in association with several integral and peripheral membrane proteins, forming a complex known as the dystrophin glycoprotein complex (DGC) (Ervasti J M. et al. (1991) *Cell.* 66:1121-1131; Ibraghimov-Beskrovnaya O. et al. (1992) Nature (London); Yoshida M. et al. (1990) *J Biochem (Tokyo).* 108:748-752).

In preferred embodiments, antisense oligonucleotides are used to prevent or treat diseases or disorders associated with DMD family members. Exemplary Dystrophin family mediated diseases and disorders which can be treated with cell/tissues regenerated from stem cells obtained using the antisense compounds comprise: a muscle disease or disorder (e.g., Muscular dystrophy including Duchenne's muscular dystrophy, Becker's muscular dystrophy, Spinal bulbar muscular atrophy, dystrophinopathy, sarcoglycanopathy, limb girdle muscular dystrophy, congenital muscular dystrophy, congenital myopathy, distal myopathy. Symptomatic form of muscular dystrophy of Duchenne and Becker in female carriers myotonic syndrome etc.; a muscle-wasting disease), a neurological disease or disorder (including a neuromuscular disease or disorder e.g., dystonia, myoclonus-dystonia syndrome, etc) a disease or disorder associated with altered level of dystrophin or dystrophin DAPC-complex. Left ventricular noncompaction, cancer, a cardiovascular disease or disorder, cardiomyopathy (e.g., sporadic dilated cardiomyopathy, X-linked Dilated Cardiomyopathy (XLDC) etc.), atherosclerosis a cytoskeletal disorder, congenital stationary night blindness and loss of hearing.

In a preferred embodiment, the oligonucleotides are specific for polynucleotides of DMD family, which includes, without limitation noncoding regions. The DMD family targets comprise variants of DMD family; mutants of DMD family, including SNPs; noncoding sequences of DMD family; alleles, fragments and the like. Preferably the oligonucleotide is an antisense RNA molecule.

In accordance with embodiments of the invention, the target nucleic acid molecule is not limited to DMD family polynucleotides alone but extends to any of the isoforms, receptors, homologs, non-coding regions and the like of DMD family.

In another preferred embodiment, an oligonucleotide targets a natural antisense sequence (natural antisense to the coding and non-coding regions) of DMD family targets, including, without limitation, variants, alleles, homologs, mutants, derivatives, fragments and complementary sequences thereto. Preferably the oligonucleotide is an antisense RNA or DNA molecule.

In another preferred embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound. These compounds are then tested using the methods described herein to determine their ability to inhibit expression of a target nucleic acid.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target, nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc. is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another preferred embodiment, targeting of DMD family including without limitation, antisense sequences which are identified and expanded, using for example, PCR, hybridization etc., one or more of the sequences set forth as SEQ ID NO: 3 to 7, and the like, modulate the expression or function of DMD family. In one embodiment, expression or function is up-regulated as compared to a control. In another preferred embodiment, expression or function is down-regulated as compared to a control.

In another preferred embodiment, oligonucleotides compose nucleic acid sequences set forth as SEQ ID NOS: 8 to 22 including antisense sequences which arc identified, and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another preferred embodiment, the nucleotides comprise a phosphorus derivative. The phosphorus derivative (or modified phosphate group) which may he attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with die identification of a target nucleic acid, whose function is to be modulated. This target nucleic acid may be, for example, a cellular gene (or mRNA transcribed from the gene) whose expression is associated with a particular disorder or disease state, or a nucleic acid molecule from an infections agent, in the present invention, the target nucleic acid encodes Dystrophin family.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion, of the target nucleic acid having at least one identifiable structure, function, or characteristic. Within regions of target nucleic acids are segments, "Segments" are defined as smaller or sub-portions of regions within a target nucleic acid. "Sites," as used in the present invention, are defined as positions within a target nucleic acid.

In a preferred embodiment, the antisense oligonucleotides bind to the natural antisense sequences of Dystrophin family and modulate the expression and/or function of Dystrophin family (SEQ ID NO: 1 and 2). Examples of antisense sequences include SEQ ID NOS: 3 to 22.

In another preferred embodiment, the antisense oligonucleotides bind to one or more segments of Dystrophin family polynucleotides and modulate the expression and/or function of Dystrophin family. The segments comprise at least five consecutive nucleotides of the Dystrophin family sense or antisense polynucleotides.

In another preferred embodiment, the antisense oligonucleotides are specific for natural antisense sequences of Dystrophin family wherein binding of the oligonucleotides to the natural antisense sequences of Dystrophin family modulate expression and/or function of Dystrophin family.

In another preferred embodiment, oligonucleotide compounds comprise sequences set forth as SEQ ID NOS: 8 to 22, antisense sequences which are identified and expanded, using for example, PCR, hybridization etc These oligonucleotides can comprise one or more modified nucleotides, shorter or longer fragments, modified bonds and the like. Examples of modified bonds or intemucleotide linkages comprise phosphorothioate, phosphorodithioate or the like. In another preferred embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Dystrophin family, regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region", which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of art mRNA in the 5' direction from the translation initiation codon, and tints including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for tins invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another preferred embodiment, the antisense oligonucleotides bind to coding and/or non-coding regions of a target polynucleotide and modulate the expression and/or function of the target molecule.

In another preferred embodiment, the antisense oligonucleotides bind to natural, antisense polynucleotides and modulate the expression and/or function of the target molecule.

In another preferred embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and raRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative preferred target segments are considered to be suitable for targeting as well.

Target segments can include DNA or RNA sequences that comprise at least the 5 consecutive nucleotides from the 5'-terminus of one of the illustrative preferred target segments (the remaining nucleotides being a consecutive stretch of the same DNA or RNA beginning immediately upstream of the 5'-terminus of the target segment and continuing until the DNA or RNA contains about 5 to about 100 nucleotides). Similarly preferred target segments are represented by DNA or RNA sequences that comprise at least the 5 consecutive nucleotides from the 3'-terminus of one of the illustrative preferred target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further preferred target segments.

Once one or more target regions, segments or sites have been identified, antisense compounds are chosen which ate sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, it is preferred to target specific nucleic acids by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from, initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown, that the set of non-polyadenylated nuclear RNAs may be very large, and that many such transcripts arise from so-called intergenic regions (Cheng, J. et al. (2005) *Science* 308 (5725), 1149-1154; Kapranov, P. et al. (2005). *Genome Res* 15 (7), 987-997). The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs feat are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and mat either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the ease of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down bom antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based, mechanisms. In general, nucleic acids (including oligonucleotides) may be described as "DNA-like" (i.e., generally having one or snore 2'-deoxy sugars and, generally, T rather than U bases) or "RNA-like" (i.e., generally having one or more 2'-hydroxyl or 2'-modified sugars and, generally, U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another preferred embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs). It is currently not known whether RNAa is conserved in other organisms.

Small double-stranded RNA (dsRNA), such as small interfering RNA (siRNA) and mieroRNA (miRNA), have been found to be the trigger of an evolutionary conserved mechanism known as RNA interference (RNAi). RNAi invariably leads to gene silencing via remodeling chromatin to thereby suppress transcription, degrading complementary mRNA, or blocking protein translation. However, in instances described in detail in the examples section which follows, oligonucleotides are shown to increase the expression and/or function of the Dystrophin family polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "preferred target segments" identified herein may be employed in a screen for additional compounds that modulate the expression of Dystrophin family polynucleotides. "Modulators" are those compounds that decrease or increase the expression of a nucleic acid molecule encoding Dystrophin family and which comprise at least a 5-nucleotide portion that is complementary to a preferred target segment. The screening method comprises the steps of contacting a preferred target segment of a nucleic acid molecule encoding sense or natural antisense polynucleotides of Dystrophin family with one or more candidate modulators, and selecting for one or more candidate modulators which decrease or increase the expression of a nucleic acid molecule encoding Dystrophin family polynucleotides, e.g. SEQ ID NOS: 8 to 22. Once it is shown that the candidate modulator or modulators are capable of modulating (e.g. either decreasing or increasing) the expression of a nucleic acid molecule encoding Dystrophin family polynucleotides, the modulator may then be employed in further investigative studies of the function of Dystrophin family polynucleotides, or for use as a research, diagnostic, or therapeutic agent in accordance with the present invention.

Targeting the natural antisense sequence preferably modulates the function of the target gene. For example, the DMD family gene (e.g. accession number NM_004006 and NM_007124, FIG. 2). In a preferred embodiment, the target is an antisense polynucleotide of the DMD family gene, in a preferred embodiment, an antisense oligonucleotide targets sense and/or natural antisense sequences of Dystrophin family polynucleotides (e.g. accession number NM_004006 and NM_007124, FIG. 2), variants, alleles, isoforms, homologs, mutants, derivatives, fragments and complementary sequences thereto. Preferably the oligonucleotide is an antisense molecule and the targets include coding and noncoding regions of antisense and/or sense DMD family polynucleotides.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties maybe subject to chemical modifications (Fire et al., (1998) *Nature*, 391, 806-811; Timmons and Fire, (1998) *Nature*, 395, 854; Timmons et al., (2001) *Gene*, 263, 103-112; Tabara et al., (1998) *Science*, 282, 430-431; Montgomery et al., (1998) *Proc. Natl. Acad. Sci. USA*, 95, 15502-15507; Tuschl et al., (1999) *Genes Dev.*, 13, 3191-3197; Elbashir et al., (2001) *Nature*, 411, 494-498; Elbashir et al. (2001) *Genes Dev.* 15, 188-200). For example, such double-stranded moieties have been shown to inhibit the target by the classical hybridization of antisense strand of the duplex to the target, thereby triggering enzymatic degradation of the target (Tijsterman et. al., (2002) *Science*, 295, 694-697).

In a preferred embodiment, an antisense oligonucleotide targets Dystrophin family polynucleotides (e.g. accession number NM_004006 and NM_007124), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Dystrophin family alone but extends to any of the isoforms, receptors, homologs and the like of Dystrophin family molecules.

In another preferred embodiment, an oligonucleotide targets a natural antisense sequence of DMD family polynucleotides, for example, polynucleotides set forth as SEQ ID NO: 3 to 7, and any variants, alleles, homologs, mutants, derivatives, fragments and complementary sequences thereto. Examples of antisense oligonucleotides are set forth as SEQ ID NOS: 8 to 22.

In one embodiment, the oligonucleotides are complementary to or bind to nucleic acid sequences of Dystrophin family antisense, including without limitation noncoding sense and/or antisense sequences associated with Dystrophin family polynucleotides and modulate expression and/or function of Dystrophin family molecules.

In another preferred embodiment, the oligonucleotides are complementary to or bind to nucleic acid, sequences of DMD family natural antisense, set forth as SEQ ID NO: 3 to 7 and modulate expression and/or function of DMD family molecules.

In a preferred embodiment, oligonucleotides comprise sequences of at least 5 consecutive nucleotides of SEQ ID NOS: 8 to 22 and modulate expression and/or function of Dystrophin family molecules.

The polynucleotide targets comprise DMD family, including family members thereof, variants of DMD family; mutants of DMD family, including SNPs; noncoding sequences of DMD family; alleles of DMD family; species variants, fragments and the like. Preferably the oligonucleotide is an antisense molecule.

In another preferred embodiment, the oligonucleotide targeting Dystrophin family polynucleotides, comprise: antisense RNA, interference RNA (RNAi), short interfering RNA (siRNA): micro interfering RNA (miRNA); a small, temporal RNA (stRNA); or a short, hairpin RNA (shRNA); small RNA-induced gene activation (RNAa); or, small activating RNA (saRNA).

In another preferred embodiment, targeting of Dystrophin family polynucleotides, e.g. SEQ ID NO: 3 to 7, modulates the expression or function of these targets. In one embodiment, expression or function is up-regulated, as compared to a control. In another preferred embodiment, expression or function is down-regulated as compared to a control.

In another preferred embodiment, antisense compounds comprise sequences set forth as SEQ ID NOS: 8 to 22. These oligonucleotides can comprise one or more modified nucleotides, shorter or longer fragments, modified bonds and the like.

In another preferred embodiment, SEQ ID NOS: 8 to 22 comprise one or mote LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedlv cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech 240 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, (1995) *Ann. Rep. Med. Chem.* 30, 285-294; Christoffersen and Marr, (1995) *J. Med. Chem.* 38, 2023-2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound, to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, (1979) *Proc. R. Soc. London*, B 205, 435) have been used to evolve new nucleic acid catalysts capable of catalyzing a variety of reactions, such as cleavage and ligation of phosphodiester linkages and amide linkages, (Joyce, (1989) *Gene*, 82, 83-87; Beaudry et al., (1992) *Science* 251, 635-641: Joyce, (1992) *Scientific American* 267, 90-97; Breaker et al., (1994) *TIBTECH* 12, 268: Bartel et al., (1993)

Science 261:1411-1418; Szostak, (1993) *TIBS* 17, 89-93; Kumar et al., (1995) *FASEB J.*, 9, 1183; Breaker, (1996) *Curr. Op. Biotech.*, 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self cleaving ribozymes. It is then possible that the structures of certain selfcleaving ribozymes may be optimized to give maximal catalytic activity, or that entirely new RNA motifs can be made that display significantly fester rates for RNA phosphodiester cleavage.

Intermolecular cleavage of an RNA substrate by an RNA catalyst that fits the 'hammerhead' model was first shown in 1987 (Uhlenbeek, O. C. (1987) *Nature*, 328: 596-600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, (1988) *Nature*, 334, 585; Walbot and Bruening, (1988) *Nature*, 334, 196; Uhlenbeck, O. C. (1987) *Nature*, 328: 596-600; Koizumi, M., et al. (1988) *FEBS Lett.*, 228: 228-230). This has allowed use of the catalytic RNA to cleave specific target sequences and indicates that catalytic RNAs designed according to the "hammerhead" model may possibly cleave specific substrate RNAs in vivo, (see Haseloff and Gerlach, (1988) *Nature*, 334, 585; Walbot and Bruening, (1988) *Nature*, 334, 196; Uhlenbeck, O. C. (1987) *Nature*, 328: 596-600).

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and. permit foe use of regulated and tissue specific promoters for gene expression.

In a preferred embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be numerics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleotide linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines (Hammond et al., (1991) *Nat. Rev. Genet.*, 2, 110-119; Matzke et al. (2001) *Curr. Opin. Genet. Dev.*, 11, 221-227; Sharp, (2001) *Genes Dev.*, 15, 485-490). When formed from two strands, or a single strand that takes the form of a self-complementaty hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DMA-like" (i.e., generally having one or more 2'-deoxy sugars and, generally, T rather than T bases) or "RNA-like" (i.e., generally having one or more 2'- hydroxyl or 2'-modified sugars and, generally U ranter than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that, this embodies antisense compounds having antisense portions of 12, 13, 14, 15, 16 17, 18, 19, 20, 21, 22, 23, 24, 25, 26, 27, 28, 29 or 30 nucleotides in length, or any range therewithin.

In another preferred embodiment, the oligomeric compounds of the present invention, also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99%, or about 100%.

In another preferred embodiment, the antisense oligonucleotides, such as for example, nucleic acid molecules set forth in SEQ ID NOS: 3 to 22 comprise one or more substitutions or modifications. In one embodiment, the nucleotides are substituted with locked nucleic acids (LNA).

In another preferred embodiment, the oligonucleotides target one or more regions of the nucleic acid molecules sense and/or antisense of coding and/or non-coding sequences associated with DMD family and the sequences set forth as SEQ ID NOS: 1, 2 and 3 to 7. The oligonucleotides are also targeted to overlapping regions of SEQ ID NOS: 1, 2 and 3 to 7.

Certain preferred oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonceleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also beers referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another preferred embodiment, the region of the oligonucleotide which is modified comprises at least one nucleotide modified, at the 2' position of the sugar, most preferably a 2'-Oalkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA, Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification ate presently more preferred. In some cases, oligonucleotide modifications which enhance target binding affinity are also, independently, able to enhance nuclease resistance. Some desirable modifications can be found in De Mesmaeker et al. (1995) *Acc. Chem. Res.*, 28:366-374.

Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, —N(CH3)-O—CH2 [as a methylene(methylimino) or MMI backbone], CH2-O—N (CH3)-CH2, CH2-N (CH3)-N (CH3)-CH2 and O—N (CH3)-CH2-H2 backbones, wherein the native phosphodiester backbone is represented as O—P—O—CH). The amide backbones disclosed by De Mesmaeker et al. (1995) *Acc. Chem. Res.* 28:366-374 are also preferred. Also preferred are oligonucleotides having morpholino backbone structures (Summerton and Weller, U.S. Pat. No. 5,034, 506). In other preferred embodiments, such as the peptide nucleic acid (PNA) backbone, the phosphodiester backbone of the oligonucleotide is replaced with a poiyamide backbone, the nucleotides being bound directly or indirectly to the aza nitrogen atoms of the poiyamide backbone (Nielsen et al. (1991) *Science* 254, 1497). Oligonucleotides may also comprise one or more substituted sugar moieties. Preferred oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynatnic properties of an oligonucleotide and other substituents having similar properties. A preferred modification includes 2,-methoxyethoxy [2'-O-CH2 CH2 OCH3, also known as 2'-O-(2-methoxyethyl)] (Martin et al., (1995) *Helv. Chim. Acta*, 78, 486). Other preferred modifications include 2'-methoxy (2'-O-CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolyalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W. H. Freeman & Co., San Francisco, 1980, pp 75-77; Gebeyehu, G., (1987) et al. *Nucl. Acids Res.* 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T, and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger el al., (1989) *Proc. Nad Acad. Sci. USA* 86, 6553), cholic acid (Manoharan et al. (1994) *Bioorg. Med. Chem. Let.* 4,1053), a thioether, e.g., hexyl-S-tritylthiol (Manoharan et al. (1992) *Ann. N.Y. Acad. Sci.* 660, 306; Manoharan et al. (1993) *Bioorg. Med. Chem. Let.* 3, 2765), a thiocholesterol (Oberhauser et al., (1992) *Nucl. Acids Res.* 20, 533), an aliphatic chain, e.g., dodecandiol or undecyl residues (Saison-Behmoaras el at. EMBO J. 1991, 10, 111; Kabanov et al. (1990) *FEBS Lett* 259, 327; Svinarchuk et al. (1993) *Biochimie* 75, 49), a phospholipid, e.g., di-hexadecyl-rac-glycerol or triemylammonium 1,2-di-O-hexadecyl-rac-glycero-3-H-phosphonate (Manoharan et al. (1995) *Tetrahedron Lett.* 36, 3651; Shea et al. (1990) *Nucl. Acids Res.* 18, 3777), a polyamine or a polyethylene glycol chain (Manoharan et al. (1995) *Nucleosides & Nucleotides*, 14, 969), or adamamane acetic acid (Manoharan et al. (1995) *Tetrahedron Lett.* 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinyiated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (Uhlman, et al. (2000) *Current Opinions in Drug Discovery & Development* Vol. 3 No 2). This can be achieved by substituting some of the monomers in the current oligonucleotides by LNA monomers. The LNA modified oligonucleotide may have a size similar to the parent compound or may be larger or preferably smaller. It is preferred that such LNA-modified oligonucleotides contain less than about 70%, more preferably less than about 60%, roost preferably less than about 50%, LNA monomers and that their sizes are between about 5 and 25 nucleotides, more preferably between about 12 and 20 nucleotides.

Preferred modified oligonucleotide backbones comprise, but not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3-5' to 5'-3' or 2-5' to 5-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,1.31; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomie or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethyglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) *Science* 254, 1497-1500.

In another preferred emtodiment of the invention the oligonucleotides with phosphorothioate backbones and oligonucleosides with heteroatom backbones, and in particular —$CH_2$-NH—O—$CH_2$-, —$CH_2$-N ($CH_3$)-O—$CH_2$- known as a methylene (methylimino) or MMI backbone, —$CH_2$-O—N ($CH_3$)-$CH_2$-, —$CH_2$N($CH_3$)-N($CH_3$)$CH_2$- and —O—N($CH_3$)-$CH_2$-$CH_2$- wherein the native phosphodiester backbone is represented as —O—P—O—$CH_2$- of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034, 506.

Modified oligonucleotides may also contain one or more substituted sugar moieties. Preferred oligonucleotides comprise one of the following at the 2' position: OH; F; O—, S—, or N-alkyl; O—,S—, or N-alkenyl; O—, S— or N-alkynyl; or O alkyl-O-alkyl wherein the alkyl, alkenyl and alkynyl may be substituted or unsubstituted C to CO alkyl or C2 to CO alkenyl and alkynyl. Particularly preferred are $O(CH_2)$nOm$CH_3$, $O(CH_2)$n, $OCH_3$, $O(CH_2)$n$NH_2$, $O(CH_2)$n$CH_3$, $O(CH_2)$n$ONH_2$, and $O(CH_2nON(CH_2)nCH_3)_2$ where n and m can be from 1 to about 10. Other preferred oligonucleotides comprise one of the following at the 2' position: C to CO, (lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocyloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification comprises 2'-methoxyethoxy (2'-O—$CH_2CH_2OCH_3$, also known as 2'-O-(2-methoxyethyl) or 2'-MOE) (Martin et al., (1995) *Helv. Chim. Acta*, 78, 486-504) i.e., an alkcoxyalkoxy group. A further preferred modification comprises 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O-$CH_2$-O—$CH_2$-N ($CH_2$)2.

Other preferred modifications comprise 2'-methoxy (2'-O $CH_3$), 2'-aminopropoxy (2'-O $CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,148,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucieobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthrae, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Krosohwitz, J. I., ed. John Wiley & Sons, 1990, those disclosed by Englisch et al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine, 5-methylcytosine substitutions have been shown to increase nucleic acid duplex stability by 0.6-1.2° C. (Sanghvi, Y. S., Crooke, S. T, and Leb;eu, B., eds. 'Antisense Research and Applications', CRC Press, Boca Raton, 1993, pp. 276-278) and are presently preferred base substitutions, even more particularly when combined with 2-Omethoxyethyl sugar modifications.

Representative United States patents that teach the preparation of the above noted modified nucleotides as well as other modified nucleotides comprise, but are not limited to, U.S. Pat. Nos. 3,687,808, as well as 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety (Letsinger et al., (1989) Proc. Natl. Acad. Sci. USA, 86, 6553-6556), cholic acid (Manoharan et al., (1994) Bioorg. Med. Chem. Let., 4, 1053-1060), a thioether, e.g., hexyl-S-tritylthiol (Manoharan et al., (1992) Ann. N. Y. Acad. Sci, 660, 306-309: Manoharan et al., (1993) Bioorg. Med. Chem. Let., 3, 2765-2770), a thiocholesterol (Oberhauser et al., (1992) Nucl. Acids Res., 20, 533-538), an aliphatic chain, e.g., dodecandiol or undecyi residues (Kabanov et al., (1990) FEBS Lett., 259, 327-330; Svinarchuk et al., (1993) Biochimie 75, 49-54), a phospholipid, e.g., di-hexadecyl-rac-glycerol or triethyianimonium 1,2-ds-O-hexadecyl-rac-glycero-3-H-phosphonate (Manoharan et al., (1995) Tetrahedron Lett., 36, 3651-3654; Shea et al., (1990) Nucl. Acids Res., 18, 3777-3783), a polyamine or a polyethylene glycol chain (Mancharan et al., (1995) Nucleosides & Nucleotides, 14, 969-973), or adamantane acetic acid (Manoharan et al., (1995) Tetrahedron Lett., 36, 3651-3654), a palmityl moiety (Mishra et al. (1995) Biochem. Biophys. Acta, 1264, 229-237), or an octadecylamine or hexylaminocarbonyl-t oxycholesterol moiety (Crooke et al., (1996) J. Pharmacol. Exp. Ther., 277, 923-937).

Representative United States patents that teach the preparation of such oligonucleotides conjugates comprise, but are not limited to, U.S. Pat. Nos. 4,828,979; 4,948,882; 5,218,105: 5,525,465; 5,541,313; 5,545,730: 5,552,538; 5,578,717, 5,580,731; 5580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and preferred target segments identified herein in drug discovery efforts to elucidate relationships that exist between Dystrophin family polynucleotides and a disease state, phenotype, or condition. These methods include detecting or modulating Dystrophin family polynucleotides comprising contacting a sample, tissue, cell, or organism, with the compounds of the present invention, measuring the nucleic acid or protein level of Dystrophin family polynucleotides and/or a related phenotype or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of foe exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing foe effector RNA. Based on sequence conservation, primers can be designed and used to amplify coding regions of the target genes. Initially, the most highly expressed coding region from each gene cart be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3'non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransfetase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

DMD family protein and mRNA expression can be assayed using methods known to those of skill in the art and described elsewhere herein. For example, immunoassays such as the ELISA can be used to measure protein levels. DMD family antibodies for ELISAs are available commercially, e.g., from Abnova, (Walnut, Calif.), Abcam, Cambridge, Mass.

In embodiments, DMD family expression (e.g., mRNA or protein) in a sample (e.g., cells or tissues in vivo or in vitro) treated using an antisense oligonucleotide of the invention is evaluated by comparison with DMD family expression in a control sample. For example, expression of the protein or nucleic acid can be compared using methods known to those of skill in the art with that in a mock-treated or untreated sample. Alternatively, comparison with a sample treated with a control antisense oligonucleotide (e.g., one having an altered or different sequence) can be made depending on the information desired. In another embodiment, a difference in the expression of the DMD family protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of DMD family mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of DMD family mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6,5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression, with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the Dystrophin family genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.*, 480,17-24; Celis, et al., (2000) *FEBS Lett.*, 480, 2-16), SAGE (serial analysis of gene expression) (Madden, et al., (2000) Drug Discov. Today, 5,4 15-425), READS (restriction enzyme amplification of digested cDNAs) (Prashar and Weissman, (1999) *Methods Enzymol.*, 303, 258-72), TOGA (total gene expression analysis) (Sutcliffe, et al., (2000) *Proc. Natl. Acad. Sci. U.S.A.*, 97, 1976-81), protein arrays and proieomies (Celis, et al., (2000) *FEBS Lett.*, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol. 2000, 80, 143-57), subtractive RNA fingerprinting (SuRF) (Fuchs, et al., (2000) Anal. Biochem. 286, 91-98; Larson, et al., (2000) *Cytometry* 41, 203-208), subtractive cloning, differential display (DD) (Jurecic and Belmont, (2000) *Curr. Opin. Microbiol.* 3, 316-21), comparative genomic hybridization. (Carulli, et al., (1998) *J. Cell Biochem. Suppl.*, 31, 286-96), FISH (fluorescent in situ hybridization) techniques (Going and Gusterson, (1999) *Eur. J. Cancer,* 35, 1895-904) and mass spectrometry methods (To, Comb. (2000) *Chem. High Throughput Screen,* 3, 235-41).

The compounds of the invention are useful for research and diagnostics, because these compounds hybridize to nucleic acids encoding Dystrophin family. For example, oligonucleotides that hybridize with such efficiency and under such conditions as disclosed herein as to be effective Dystrophin family modulators are effective primers or probes under conditions favoring gene amplification or detection, respectively. These primers and probes are useful in methods requiring the specific detection of nucleic acid molecules encoding Dystrophin family and in the amplification of said nucleic acid molecules for detection or for use in further studies of Dystrophin family. Hybridization of the antisense oligonucleotides, particularly the primers and probes, of the invention with a nucleic acid encoding Dystrophin family can be detected by means known in the art. Such means may include conjugation of an enzyme to the oligonucleotide, radiolabeling of the oligonucleotide, or any other suitable detection means. Kits using such detection means for detecting the level of Dystrophin family in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of Dystrophin family polynucleotides is treated, by administering antisense compounds in accordance with this invention. For example, in one non-limiting embodiment, the methods comprise the step of administering to the animal in need of treatment, a therapeutically effective amount of Dystrophin family modulator. The Dystrophin family modulators of the present invention effectively modulate the activity of the Dystrophin family or modulate the expression of the Dystrophin family protein. In one embodiment, the activity or expression of Dystrophin family in an animal is inhibited by about 10% as compared to a control. Preferably, the activity or expression of Dystrophin family in an animal is inhibited by about 30%. More preferably, the activity or expression of Dystrophin family in an animal is inhibited by 50% or more. Thus, the oligomeric compounds modulate expression of Dystrophin family mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of Dystrophin family and/or in an animal is increased by about 10% as compared to a control. Preferably, the activity or expression of Dystrophin family in an animal is increased by about 30%, More preferably, the activity or expression of Dystrophin family in an animal is increased by 50% or more. Thus, the oligomeric compounds modulate expression of Dystrophin family mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of Dystrophin family may be measured in serum, blood, adipose tissue, liver or any other body fluid, tissue or organ of the animal. Preferably, the cells contained within said fluids, tissues or organs being analyzed contain a nucleic acid molecule encoding Dystrophin family peptides and/or the Dystrophin family protein itself.

The compounds of the invention can be utilized in pharmaceutical compositions by adding an effective amount of a compound to a suitable pharmaceuticaily acceptable diluent or carrier. Use of the compounds and methods of the invention may also be useful prophylactically.

Conjugates

Another modification of the oligonucleotides of the invention involves chemically linking to the oligonucleotide one or more moieties or conjugates that enhance the activity, cellular distribution, or cellular uptake of the oligonucleotide. These moieties or conjugates can include conjugate groups covalently bound to functional groups such as primary or secondary hydroxy groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen, sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5- tritylthiol, a thiocholesterol, an aliphatic chain, e.g., dodecandiol or undecyl residues, a phospholipid, e.g., di-hexadecyl-rac-glycerol or triethylammonium 1,2-di-O-hexadeeyl-rac-glycero-3-Hphosphonate, a polyamine or a polyethylene glycol chain, or adamantane acetic acid, a palmityl moiety, or an octadecylamine or hexylamino-carbonyl-oxy-cholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamine acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016;

5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295: 5,527,528; 5,534,259: 5,543,152; 5,556,948; 5,580,575; and 5,595,756, each of which is herein incorporated by reference, Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired ease.

In an embodiment, invention, practice involves administering at least one of the foregoing antisense oligonucleotides with a suitable nucleic acid delivery system. In one embodiment, that system includes a non-viral vector operably linked to the polynucleotide. Examples of such nonvirai vectors include the oligonucleotide alone (e.g. any one or more of SEQ ID NOS: 8 to 22) or in combination with a suitable protein, polysaccharide or lipid formulation.

Additionally suitable nucleic acid delivery systems include viral vector, typically sequence from at least one of an adenovirus, adenovirus-associated vims (AAV), helper-dependent adenovirus, retrovirus, or hemagglutinatin virus of Japan-liposome (HVJ) complex. Preferably, the vital vector comprises a strong eukaryotic promoter operably linked to the polynucleotide e.g., a cytomegalovirus (CMV) promoter.

Additionally preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector [Geller, A. I. et al., (1995) *J. Neurochem,* 64: 487; Lim, F., et al., in DNA Cloning: Mammalian Systems, D. Glover, Ed. (Oxford Univ. Press, Oxford England) (1995); Geller, A. I. et al., (1993) *Proc Natl. Acad Sci.:* U.S.A.:90 7603: Geller, A. I. et al., (1990) *Proc Natl. Acad. Sci USA:* 87:1149], Adenovirus Vectors (LeGal LaSalle et al., Science, 259:988 (1993); Davidson, et al., (1993) *Nat. Genet.* 3; 219; Yang, et al., (1995) *J. Virol.* 69: 2004) and Adeno-associatal Virus Vectors (Kaplitt, M. G., et al., (1994) *Nat. Genet.* 8:1.48).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutical acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may he administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal, and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered, to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or plianiiacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitoL myo-inositol, L(−) fructose, D(−) mannitol, D(+) glucose, D(+) arabinose, D(+) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through rite blood-brain barrier," and U.S. Pat. No. 6,936,589, "Parenteral delivery systems," all incorporated herein by reference in their entirety, The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTTN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharrnaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carriers) or excipieiit(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients, Emulsions are typically heterogeneous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphophilic lipids arranged in a spherical bilayer or bilayers. Liposomes are unilamellar or multilamellar vesicles which have a membrane formed from a lipophilic material and art aqueous interior that contains the composition to be delivered. Cationic liposomes are positively charged liposomes that are believed to interact with negatively charged DNA molecules to form a stable complex. Liposomes that are pH-sensittve or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize mat formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to eatsonic lipids. Preferred fatty acids and esters, pharmaceutically acceptable salts thereof, and their uses are further described in U.S. Pat. No. 6,287,860.

Compositions and formulations for oral administration, include powders or granules, microparticulates, nanoparticulates, suspensions or solutions in water or non-aqueous media, capsules, gel capsules, sachets, tablets or minitablets. Thickeners, flavoring agents, diluents, emulsifies, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described, in U.S. Pat. No. 6,287,860, which is incorporated herein by reference. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexeet to form micro or nanoparticles.

Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oiigomeric compounds and one or more other chemotherapeutic agents that function by a non-antisense mechanism. Examples of such chemotherapeutic agents include but are not limited to cancer chemotherapeutic drags such as daunorubican, daunomycin, dactinomycin, doxorubicin, epirubicin, idarubicin, esorubicin, bleomycin, mafosfamide, ifosfamide, cytosine arabinoside, bischoroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of Dystrophin family, and the second target may be a region from another nucleotide sequence. Alternatively, compositions of the invention may contain two or more antisense compounds targeted to different regions of the same Dystrophin family nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.0.1 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of bodv weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated, herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. Ail publications and patent documents cited in this application are incorporated by reference for all purposes to the same extent as if each individual publication or patent document were so individually denoted. By their citation of various references in this document. Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Design of Antisense Oligonucleotides Specific for a Nucleic Acid Molecule Antisense to a Dystrophin Family and/or a Sense Strand of Dystrophin Family Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used, to compare nucleic acid sequences obtained, for example, by searching databases such as GenBank or by sequencing PCR products. Comparison of nucleic acid sequences from a range of species allows the selection of nucleic acid sequences that display an appropriate degree of identity between species, in the case of genes that have not been sequenced. Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the ease of in vivo assays or therapeutic treatment, and under conditions in which assays are performed in the case of in vitro assays.

The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined, by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of DMD Family Polynucleotides

Treatment of 518A2 Cells with Antisense Oligonucleotides

518A2 cells obtained from Albert Einstein-Montefiore Cancer Center, NY were grown in growth media (MEM/EBSS (Hyclone cat#SH30024, or Mediatech cat#MT-10-010-CV)+10% FBS (Mediatech cat#MT35-011-CV)+penicillin/streptomycin (Mediatech cat#MT30-002-CI)) at 37° C. and 5% $CO_2$. One day before the experiment the cells were reflated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat#31985-070) and 4 μl of Lipofectamine 2000 (Invitrogen cat#11668019) at room temperature for 20 min and applied to each well of the 6 well plates with 518A2 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat#23105) or RNeasy Total RNA Isolation kit from Qiagen (cat#74181) following the manufacturers' instructions. 600 ng of RNA was added to the reverse transcription reaction performed using Verso cDNA kit from Thermo Scientific (cat#AB1453B) or High Capacity cDNA Reverse Transcription Kit (cat#4368813 as described in the manufacturer's protocol. The cDNA from this reverse transcription reaction was used to monitor gene expression by real time PCR using ABI Taqman Gene Expression Mix (cat#4369510) and primers/probes designed by ABI (Applied Biosystems Taqman Gene Expression Assay; Hs00187805_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Figures 1C, 2:
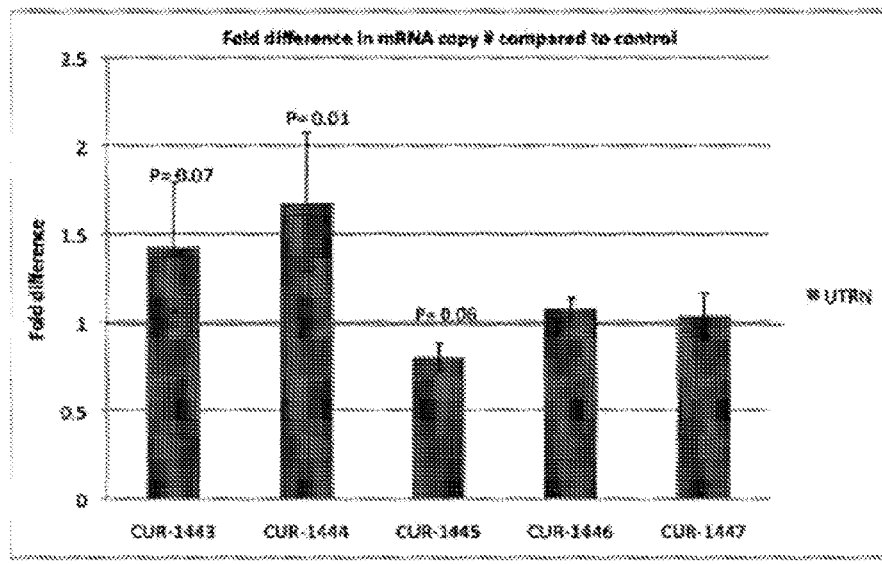
FIG. 1C is a graph, of real time PCR results showing the fold change+standard deviation in UTRN mRNA after treatment of MCF-7 cells with phosphorothioate oligonucleotides introduced using Lipofectamine 2000, as compared to control. Bars denoted as CUR-1443 to CUR-1447 correspond to samples treated with SEQ ID NOS: 18 to 22 respectively.
FIG. 2 shows

Results: Real time PCR results show that the levels of DMD family mRNA in 518A2 cells are significantly increased 48 h after treatment with two of the siRNAs designed to DMD family antisense BG208074. Treatment with siRNAs to other antisense molecules, BF838561, BF768753 and BF950643, did not elevate DMD family mRNA levels (FIGS. 1A and B).

Treatment of MCF-7 Cells with Antisense Oligonucleotides

MCF-7 cells from ATCC (cat#HTB-22) were grown in growth media (MEM/EBSS (Hyclone cat #SH30024, or Mediatech cat#MT-10-010-CV)+10% FBS (Mediatech cat#MT35-011-CV)+penicillin/streptomycin (Mediatech cat#MT30-002-CI)) at 37° C. and 5% CO2. One day before the experiment the cells were replated at the density of 1.5× $10^5$/ml into 6 well plates and incubated at 37° C. and 5% CO2 On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat#31985-070) and 4 μl of Lipofectamine 2000 (Invitrogen cat#11668019) at room temperature for 20 min and applied to each well of the 6 well plates with MCF-7 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat#23105) or RNeasy Total RNA Isolation kit from Qiagen (cat#74181) following the manufacturers' instructions. 600 ng of RNA was added to the reverse transcription reaction performed using Verso cDNA kit from Thermo Scientific (cat#AB1453B) or High Capacity cDNA Reverse Transcription Kit (cat#4368813) as described in the manufacturer's protocol. The cDNA from this reverse transcription reaction, was used to monitor gene expression by real time PCR using ABI Taqman Gene Expression Mix (cat#4369510) and primers/probes designed by ABI (Applied Biosystems Taqman Gene Expression Assay: Hs01126016_m1 by Applied Biosystems Inc., Foster City Calif.). The following PCR cycle was used: 50° C. for 2 min, 95° C. for 10 minl, 40 cycles of (95° C. for 15 seconds, 60° C. for 1 min) using Mx4000 thermal cycler (Stratagene) or StepOne Plus Real Time PCR Machine (Applied Biosystems).

Fold change in gene expression after treatment with antisense oligonucleotides was calculated based on the difference in 18S-normalized dCt values between treated and mock-transfected samples.

Results: Real time PCR results show that the levels of UTRN mRNA in MCF-7 cells are significantly increased 48 h after treatment with siRNAs designed to UTRN family antisense ENST00000431309.

Although the invention has been illustrated and described with respect to one or more implementations, equivalent alterations and modifications will occur to others skilled in the art upon foe reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain foe nature of the technical disclosure. It is submitted with the understanding that it will not be used to interpret or limit the scope or meaning of the following claims.

What is claimed is:

1. A method of upregulating a function of and/or the expression of a Dystrophin family polynucleotide selected from SEQ ID NO 2 or a polyuncleotide encoding such a sequence in patient cells or tissues in vivo or in vitro comprising: contacting said cells or tissues with at least one antisense oligonucleotide of about 15-30 nucleotides in length that is complementary to and specifically hybridizable with a 15-30nucleotide region of a natural antisense polynucleotide; of the UTRN Dystrophin family polynucleotide; thereby upregulating a function of and/or the expression of the Dystrophin family polynucleotide in patient cells or tissues in vivo or in vitro.

2. The method of claim 1, wherein a function of and/or the expression of the Dystrophin family polynucleotide is increased in vivo or in vitro with respect to a control.

3. The method of claim 1, wherein the at least one antisense oligonucleotide targets a natural antisense sequence of a Dystrophin family polynucleotide selected from the group consisting of SEQ NO 7.

4. The method of claim 1, wherein the at least one antisense oligonucleotide targets a natural antisense oligonucleotide antisense to coding and/or non-coding nucleic acid sequences of a Dystrophin family polynucleotide.

5. The method of claim 1, wherein the at least one antisense oligonucleotide targets a natural antisense oligonueleotide having overlapping and/or non-overlapping sequences with a Dystrophin family polynucleotide.

6. The method of claim 1, wherein the at least one antisense oligonucleotide comprises one or more modifications selected from: at least one modified sugar moiety, at least one modified internucleoside linkage, at least one modified nucleotide, and combinations thereof.

7. The method of claim 6, wherein the one or more modifications comprise at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and combinations thereof.

8. The method of claim 6, wherein the one or more modifications comprise at least one modified internucleoside linkage selected from: a phosphorodithioate, alkylphosphonate, phosphorodithioate, alkylphosphonothioate, phosphoramidate, carbamate, carbonate, phosphate triester, aectamidate, carboxymethyl ester, and combinations thereof.

9. The method of claim 6, wherein the one or more modifications comprise at least one modified nucleotide selected from: a peptide nucleic acid (PNA), a locked nucleic acid (LNA), an arabino-nucleic acid (FANA), an analogue, a derivative, and combinations thereof.

10. The method according to claim 1, wherein the natural antisense oligonucleotide is SEQ ID NO: 7.

11. The method of claim 1, wherein the at least one oligonucleotide comprises at least one oligonucleotide sequences set forth as SEQ ID NOS: 18 and 19.

* * * * *

SEQUENCE LISTING

```
<160> NUMBER OF SEQ ID NOS: 32

<210> SEQ ID NO 1
<211> LENGTH: 13993
<212> TYPE: DNA
<213> ORGANISM: Homo sapiens
<300> PUBLICATION INFORMATION:
<308> DATABASE ACCESSION NUMBER: NM_004006
<309> DATABASE ENTRY DATE: 2010-08-04
<313> RELEVANT RESIDUES IN SEQ ID NO: (1)..(13993)

<400> SEQUENCE: 1
tcctggcatc agttactgtg ttgactcact cagtgttggg atcactcact ttcccctac      60 aggactcaga tctgggaggc aattaccttc ggagaaaaac gaataggaaa aactgaagtg    120 ttacttttt taaagctgct gaagtttgtt ggtttctcat tgtttttaag cctactggag    180
caataaagtt tgaagaactt ttaccaggtt ttttttatcg ctgccttgat atacactttt    240
caaaatgctt tggtgggaag aagtagagga ctgttatgaa agagaagatg ttcaaaagaa    300
aacattcaca aaatgggtaa atgcacaatt ttctaagttt gggaagcagc atattgaaa     360 cctcttcagt gacctacagg atgggaggcg cctcctagac ctcctcgaag gcctgacagg    420
gcaaaaactg ccaaaagaaa aaggatccac aagagttcat gccctgaaca atgtcaacaa    480
ggcactgcgg gttttgcaga acaataatgt tgatttagtg aatattggaa gtactgacat    540
cgtagatgga aatcataaac tgactcttgg tttgatttgg aatataatcc tccactggca    600
ggtcaaaaat gtaatgaaaa atatcatggc tggattgcaa caaaccaaca gtgaaaagat    660
```

```
tctcctgagc tgggtccgac aatcaactcg taattatcca caggttaatg taatcaactt    720
caccaccagc tggtctgatg gcctggcttt gaatgctctc atccatagtc ataggccaga    780
cctatttgac tggaatagtg tggtttgcca gcagtcagcc acacaacgac tggaacatgc    840
attcaacatc gccagatatc aattaggcat agagaaacta ctcgatcctg aagatgttga    900
taccacctat ccagataaga agtccatctt aatgtacatc acatcactct ccaagttttt    960
gcctcaacaa gtgagcattg aagccatcca ggaagtggaa atgttgccaa ggccacctaa   1020
agtgactaaa gaagaacatt ttcagttaca tcatcaaatg cactattctc aacagatcac   1080
ggtcagtcta gcacagggat atgagagaac ttcttcccct aagcctcgat tcaagagcta   1140
tgcctacaca caggctgctt atgtcaccac ctctgaccct acacggagcc catttccttc   1200
acagcatttg gaagctcctg aagacaagtc atttggcagt tcattgatgg agagtgaagt   1260
aaacctggac cgttatcaaa cagctttaga agaagtatta tcgtggcttc tttctgctga   1320
ggacacattg caagcacaag gagagatttc taatgatgtg gaagtggtga agaccagtt   1380
tcatactcat gagggggtaca tgatggattt gacagcccat cagggccggg ttggtaatat   1440
tctacaattg ggaagtaagc tgattggaac aggaaaatta tcagaagatg aagaaactga   1500
agtacaagag cagatgaatc tcctaaattc aagatgggaa tgcctcaggg tagctagcat   1560
ggaaaaacaa agcaatttac atagagtttt aatggatctc cagaatcaga aactgaaaga   1620
gttgaatgac tggctaacaa aaacagaaga agaacaagg aaaatggagg aagagccctct   1680
tggacctgat cttgaagacc taaaacgcca agtacaacaa cataaggtgc ttcaagaaga   1740
tctagaacaa gaacaagtca gggtcaattc tctcactcac atggtggtgg tagttgatga   1800
atctagtgga gatcacgcaa ctgctgcttt ggaagaacaa cttaaggtat gggagatcg   1860
atgggcaaac atctgtagat ggacagaaga ccgctgggtt cttttacaag acatccttct   1920
caaatggcaa cgtcttactg aagaacagtg ccttttttagt gcatggcttt cagaaaaaga   1980
agatgcagtg aacaagattc acacaactgg ctttaaagat caaatgaaaa tgttatcaag   2040
tcttcaaaaa ctggccgttt taaaagcgga tctagaaaag aaaaagcaat ccatgggcaa   2100
actgtattca ctcaaacaag atcttctttc aacactgaag aataagtcag tgacccagaa   2160
gacggaagca tggctggata actttgcccg tgttgggat aatttagtcc aaaaacttga   2220
aaagagtaca gcacagattt cacaggctgt caccaccact cagccatcac taacacagac   2280
aactgtaatg gaaacagtaa ctacggtgac cacaagggaa cagatcctgg taaagcatgc   2340
tcaagaggaa cttccaccac cacctcccca aaagaagagg cagattactg tggattctga   2400
aattaggaaa aggttggatg ttgatataac tgaacttcac agctggatta ctcgctcaga   2460
agctgtgttg cagagtcctg aatttgcaat ctttcggaag gaaggcaact tctcagactt   2520
aaaagaaaaa gtcaatgcca tagagcgaga aaaagctgag aagttcagaa aactgcaaga   2580
tgccagcaga tcagctcagg ccctggtgga acagatggtg aatgagggtg ttaatgcaga   2640
tagcatcaaa caagcctcag aacaactgaa cagccggtgg atcgaattct gccagttgct   2700
aagtgagaga cttaactggc tggagtatca gaacaacatc atcgctttct ataatcagct   2760
acaacaattg gagcagatga caactactgc tgaaaactgg ttgaaaatcc aacccaccac   2820
cccatcagag ccaacagcaa ttaaaagtca gttaaaaatt tgtaaggatg aagtcaaccg   2880
gctatcaggt cttcaacctc aaattgaacg attaaaaatt caaagcatag ccctgaaaga   2940
gaaaggacaa ggacccatgt tcctggatgc agactttgtg gcctttacaa atcatttaa   3000
gcaagtcttt tctgatgtgc aggccagaga gaaagagcta cagacaattt ttgacacttt   3060
```

```
gccaccaatg cgctatcagg agaccatgag tgccatcagg acatgggtcc agcagtcaga    3120
aaccaaactc tccatacctc aacttagtgt caccgactat gaaatcatgg agcagagact    3180
cggggaattg caggctttac aaagttctct gcaagagcaa caaagtggcc tatactatct    3240
cagcaccact gtgaaagaga tgtcgaagaa agcgccctct gaaattagcc ggaaatatca    3300
atcagaattt gaagaaattg agggacgctg gaagaagctc tcctcccagc tggttgagca    3360
ttgtcaaaag ctagaggagc aaatgaataa actccgaaaa attcagaatc acatacaaac    3420
cctgaagaaa tggatggctg aagttgatgt ttttctgaag gaggaatggc ctgcccttgg    3480
ggattcagaa attctaaaaa agcagctgaa acagtgcaga cttttagtca gtgatattca    3540
gacaattcag cccagtctaa acagtgtcaa tgaaggtggg cagaagataa gaatgaagc     3600 agagccagag tttgcttcga gacttgagac agaactcaaa gaacttaaca ctcagtggga    3660
tcacatgtgc caacaggtct atgccagaaa ggaggccttg aagggaggtt tggagaaaac    3720
tgtaagcctc cagaaagatc tatcagagat gcacgaatgg atgacacaag ctgaagaaga    3780
gtatcttgag agagattttg aatataaaac tccagatgaa ttacagaaag cagttgaaga    3840
gatgaagaga gctaagaag aggcccaaca aaagaagcg aaagtgaaac tccttactga      3900
gtctgtaaat agtgtcatag ctcaagctcc acctgtagca caagaggcct taaaaaagga    3960
acttgaaact ctaaccacca actaccagtg gctctgcact aggctgaatg ggaaatgcaa    4020
gactttggaa gaagtttggg catgttggca tgagttattg tcatacttgg agaaagcaaa    4080
caagtggcta aatgaagtag aatttaaact taaaaccact gaaaacattc ctggcggagc    4140
tgaggaaatc tctgaggtgc tagattcact tgaaaatttg atgcgacatt cagaggataa    4200
cccaaatcag attcgcatat tggcacagac cctaacagat ggcggagtca tggatgagct    4260
aatcaatgag gaacttgaga catttaattc tcgttggagg gaactacatg aagaggctgt    4320
aaggaggcaa aagttgcttg aacagagcat ccagtctgcc caggagactg aaaaatcctt    4380
acacttaatc caggagtccc tcacattcat tgacaagcag ttggcagctt atattgcaga    4440
caaggtggac gcagctcaaa tgcctcagga agcccagaaa atccaatctg atttgacaag    4500
tcatgagatc agtttagaag aaatgaagaa acataatcag gggaaggagg ctgcccaaag    4560
agtcctgtct cagattgatg ttgcacagaa aaaattacaa gatgtctcca tgaagtttcg    4620
attattccag aaaccagcca ttttgagca gcgtctacaa gaaagtaaga tgattttaga    4680
tgaagtgaag atgcacttgc ctgcattgga aacaaagagt gtggaacagg aagtagtaca    4740
gtcacagcta aatcattgtg tgaacttgta taaagtctg agtgaagtga agtctgaagt    4800
ggaaatggtg ataaagactg gacgtcagat tgtacagaaa aagcagacgg aaaatcccaa    4860
agaacttgat gaaagagtaa cagctttgaa attgcattat aatgagctgg gagcaaaggt    4920
aacagaaaga agcaacagt tggagaaatg cttgaaattg tcccgtaaga tgcgaaagga    4980
aatgaatgtc ttgacagaat ggctggcagc tacagatatg gaattgacaa agagatcagc    5040
agttgaagga atgcctagta atttggattc tgaagttgcc tggggaaagg ctactcaaaa    5100
agagattgag aaacagaagg tgcacctgaa gagtatcaca gaggtaggag aggccttgaa    5160
aacagttttg ggcaagaagg agacgttggt ggaagataaa ctcagtcttc tgaatagtaa    5220
ctggatagct gtcacctccc gagcagaaga gtggttaaat cttttgttgg aataccagaa    5280
acacatggaa acttttgacc agaatgtgga ccacatcaca aagtggatca ttcaggctga    5340 cacactttg gatgaatcag agaaaaagaa accccagcaa aaagaagacg tgcttaagcg    5400
```

```
tttaaaggca gaactgaatg acatacgccc aaaggtggac tctacacgtg accaagcagc    5460
aaacttgatg gcaaaccgcg gtgaccactg caggaaatta gtagagcccc aaatctcaga    5520
gctcaaccat cgatttgcag ccatttcaca cagaattaag actggaaagg cctccattcc    5580
tttgaaggaa ttggagcagt ttaactcaga tatacaaaaa ttgcttgaac cactggaggc    5640
tgaaattcag caggggtga atctgaaaga ggaagacttc aataaagata tgaatgaaga     5700
caatgagggt actgtaaaag aattgttgca agaggagac aacttacaac aaagaatcac      5760
agatgagaga agcgagagg aaataaagat aaaacagcag ctgttacaga caaaacataa      5820
tgctctcaag gatttgaggt ctcaaagaag aaaaaaggct ctagaaattt ctcatcagtg    5880
gtatcagtac aagaggcagg ctgatgatct cctgaaatgc ttggatgaca ttgaaaaaaa    5940
attagccagc ctacctgagc ccagagatga aggaaaata aaggaaattg atcgggaatt     6000
gcagaagaag aaagaggagc tgaatgcagt gcgtaggcaa gctgagggct tgtctgagga    6060
tggggccgca atggcagtgg agccaactca gatccagctc agcaagcgct ggcgggaaat    6120
tgagagcaaa tttgctcagt ttcgaagact caactttgca caaattcaca ctgtccgtga    6180
agaaacgatg atggtgatga ctgaagacat gcctttggaa atttcttatg tgccttctac    6240
ttatttgact gaaatcactc atgtctcaca agccctatta gaagtggaac aacttctcaa    6300
tgctcctgac ctctgtgcta aggactttga agatctcttt aagcaagagg agtctctgaa    6360
gaatataaaa gatagtctac aacaaagctc aggtcggatt gacattattc atagcaagaa    6420
gacagcagca ttgcaaagtg caacgcctgt ggaaagggtg aagctacagg aagctctctc    6480
ccagcttgat ttccaatggg aaaaagttaa caaaatgtac aaggaccgac aagggcgatt    6540
tgacagatct gttgagaaat ggcggcgttt tcattatgat ataaagatat ttaatcagtg    6600
gctaacagaa gctgaacagt ttctcagaaa gacacaaatt cctgagaatt gggaacatgc    6660
taaatacaaa tggtatctta aggaactcca ggatggcatt gggcagcggc aaactgttgt    6720
cagaacattg aatgcaactg gggaagaaat aattcagcaa tcctcaaaaa cagatgccag    6780
tattctacag gaaaaattgg gaagcctgaa tctgcggtgg caggaggtct gcaaacagct    6840
gtcagacaga aaaaagaggc tagaagaaca aaagaatatc ttgtcagaat tcaaagaga    6900 tttaaatgaa tttgttttat ggttggagga agcagataac attgctagta tcccacttga    6960
acctggaaaa gagcagcaac taaaagaaaa gcttgagcaa gtcaagttac tggtggaaga    7020
gttgcccctg cgccagggaa ttctcaaaca attaaatgaa actggaggac ccgtgcttgt    7080
aagtgctccc ataagcccag aagagcaaga taaacttgaa aataagctca agcagacaaa    7140
tctccagtgg ataaaggttt ccagagcttt acctgagaaa caaggagaaa ttgaagctca    7200
aataaaagac cttgggcagc ttgaaaaaaa gcttgaagac cttgaagagc agttaaatca    7260
tctgctgctg tggttatctc ctattaggaa tcagttggaa atttataacc aaccaaacca    7320
agaaggacca tttgacgttc aggaaactga aatagcagtt caagctaaac aaccggatgt    7380
ggaagagatt ttgtctaaag gcagcatttt gtacaaggaa aaaccagcca ctcagccagt    7440
gaagaggaag ttagaagatc tgagctctga gtggaaggcg gtaaaccgtt tacttcaaga    7500
gctgagggca aagcagcctg acctagctcc tggactgacc actattggag cctctcctac    7560
tcagactgtt actctggtga cacaacctgt ggttactaag gaaactgcca tctccaaact    7620
agaaatgcca tcttccttga tgttggaggt acctgctctg gcagatttca accgggcttg    7680
gacagaactt accgactggc tttctctgct tgatcaagtt ataaaatcac agagggtgat    7740
ggtgggtgac cttgaggata tcaacgagat gatcatcaag cagaaggcaa caatgcagga    7800
```

```
tttggaacag aggcgtcccc agttggaaga actcattacc gctgcccaaa atttgaaaaa    7860
caagaccagc aatcaagagg ctagaacaat cattacggat cgaattgaaa gaattcagaa    7920
tcagtgggat gaagtacaag aacaccttca gaaccggagg caacagttga atgaaatgtt    7980
aaaggattca acacaatggc tggaagctaa ggaagaagct gagcaggtct taggacaggc    8040
cagagccaag cttgagtcat ggaaggaggg tccctataca gtagatgcaa tccaaaagaa    8100
aatcacagaa accaagcagt ggccaaaga cctccgccag tggcagacaa atgtagatgt    8160
ggcaaatgac ttggccctga aacttctccg ggattattct gcagatgata ccagaaaagt    8220
ccacatgata acagagaata tcaatgcctc ttggagaagc attcataaaa gggtgagtga    8280
gcgagaggct gctttggaag aaactcatag attactgcaa cagttccccc tggacctgga    8340
aaagtttctt gcctggctta cagaagctga acaactgcc aatgtcctac aggatgctac    8400
ccgtaaggaa aggctcctag aagactccaa gggagtaaaa gagctgatga acaatggca    8460
agacctccaa ggtgaaattg aagctcacac agatgtttat cacaacctgg atgaaaacag    8520
ccaaaaaatc ctgagatccc tggaaggttc cgatgatgca gtcctgttac aaagacgttt    8580
ggataacatg aacttcaagt ggagtgaact tcggaaaaag tctctcaaca ttaggtccca    8640
tttggaagcc agttctgacc agtggaagcg tctgcaccct tctctgcagg aacttctggt    8700
gtggctacag ctgaaagatg atgaattaag ccggcaggca cctattggag gcgactttcc    8760
agcagttcag aagcagaacg atgtacatag ggccttcaag agggaattga aaactaaaga    8820
acctgtaatc atgagtactc ttgagactgt acgaatattt ctgacagagc agcctttgga    8880
aggactagag aaactctacc aggagcccag agagctgcct cctgaggaga gagcccagaa    8940
tgtcactcgg cttctacgaa agcaggctga ggaggtcaat actgagtggg aaaaattgaa    9000
cctgcactcc gctgactggc agagaaaaat agatgagacc cttgaaagac tccaggaact    9060
tcaagaggcc acggatgagc tggacctcaa gctgcgccaa gctgaggtga tcaagggatc    9120
ctggcagccc gtgggcgatc tcctcattga ctctctccaa gatcacctcg agaaagtcaa    9180
ggcacttcga ggagaaattg cgcctctgaa agagaacgtg agccacgtca atgaccttgc    9240
tcgccagctt accactttgg gcattcagct ctcaccgtat aacctcagca ctctggaaga    9300
cctgaacacc agatggaagc ttctgcaggt ggccgtcgag gaccgagtca ggcagctgca    9360
tgaagcccac agggactttg gtccagcatc tcagcacttt ctttccacgt ctgtccaggg    9420
tccctgggag agagccatct cgccaaacaa agtgccctac tatatcaacc acgagactca    9480
aacaacttgc tgggaccatc ccaaaatgac agagctctac cagtctttag ctgacctgaa    9540
taatgtcaga ttctcagctt ataggactgc catgaaactc cgaagactgc agaaggccct    9600
ttgcttggat ctcttgagcc tgtcagctgc atgtgatgcc ttggaccagc acaacctcaa    9660
gcaaaatgac cagcccatgg atatcctgca gattattaat tgtttgacca ctatttatga    9720
ccgcctggag caagagcaca caatttggt caacgtccct ctctgcgtgg atatgtgtct    9780
gaactggctg ctgaatgttt atgatacggg acgaacaggg aggatccgtg tcctgtcttt    9840
taaaactggc atcatttccc tgtgtaaagc acatttggaa gacaagtaca gatacctttt    9900
caagcaagtg gcaagttcaa caggatttg tgaccagcgc aggctgggcc tccttctgca    9960
tgattctatc caaattccaa gacagttggg tgaagttgca tcctttgggg gcagtaacat   10020
tgagccaagt gtccggagct gcttccaatt tgctaataat aagccagaga tcgaagcggc   10080
cctcttccta gactggatga gactggaacc ccagtccatg gtgtggctgc ccgtcctgca   10140
```

```
cagagtggct gctgcagaaa ctgccaagca tcaggccaaa tgtaacatct gcaaagagtg    10200
tccaatcatt ggattcaggt acaggagtct aaagcacttt aattatgaca tctgccaaag    10260
ctgctttttt tctggtcgag ttgcaaaagg ccataaaatg cactatccca tggtggaata    10320
ttgcactccg actacatcag gagaagatgt tcgagacttt gccaaggtac taaaaaacaa    10380
atttcgaacc aaaaggtatt tgcgaagca tccccgaatg ggctacctgc cagtgcagac     10440
tgtcttagag ggggacaaca tggaaactcc cgttactctg atcaacttct ggccagtaga    10500
ttctgcgcct gcctcgtccc ctcagctttc acacgatgat actcattcac gcattgaaca    10560
ttatgctagc aggctagcag aaatggaaaa cagcaatgga tcttatctaa atgatagcat    10620
ctctcctaat gagagcatag atgatgaaca tttgttaatc cagcattact gccaaagttt    10680
gaaccaggac tcccccctga ccagcctcg tagtcctgcc cagatcttga tttccttaga     10740
gagtgaggaa agaggggagc tagagagaat cctagcagat cttgaggaag aaaacaggaa    10800
tctgcaagca gaatatgacc gtctaaagca gcagcacgaa cataaaggcc tgtccccact    10860
gccgtcccct cctgaaatga tgcccacctc tccccagagt cccgggatg ctgagctcat     10920 tgctgaggcc aagctactgc gtcaacacaa aggccgcctg gaagccagga tgcaaatcct    10980
ggaagaccac aataaacagc tggagtcaca gttacagg ctaaggcagc tgctggagca     11040
accccaggca gaggccaaag tgaatggcac aacggtgtcc tctccttcta cctctctaca    11100
gaggtccgac agcagtcagc ctatgctgct ccgagtggtt ggcagtcaaa cttcggactc    11160
catgggtgag gaagatcttc tcagtcctcc ccaggacaca agcacagggt tagaggaggt    11220
gatggagcaa ctcaacaact ccttccctag ttcaagagga gaaatacccc ctggaaagcc    11280
aatgagagag gacacaatgt aggaagtctt ttccacatgg cagatgattt gggcagagcg    11340
atggagtcct tagtatcagt catgacagat gaagaaggag cagaataaat gttttacaac    11400
tcctgattcc cgcatggttt ttataatatt catcaacaa agaggattag acagtaagag     11460
tttacaagaa ataaatctat attttgtga agggtagtgg tattatactg tagatttcag     11520
tagtttctaa gtctgttatt gttttgttaa caatggcagg ttttacacgt ctatgcaatt    11580
gtacaaaaaa gttataagaa aactacatgt aaaatcttga tagctaaata acttgccatt    11640
tctttatatg gaacgcattt tgggttgttt aaaaatttat aacagttata aagaaagatt    11700
gtaaactaaa gtgtgcttta taaaaaaaag ttgtttataa aaccccctaa aaacaaaaca    11760
aacacacaca cacacacata cacacacaca cacaaaactt tgaggcagcg cattgttttg    11820
catccttttg gcgtgatatc catatgaaat tcatggcttt ttctttttt gcatattaaa     11880 gataagactt cctctaccac cacaccaaat gactactaca cactgctcat ttgagaactg    11940
tcagctgagt ggggcaggct tgagttttca tttcatatat ctatatgtct ataagtatat    12000
aaatactata gttatataga taaagagata cgaatttcta tagactgact ttttccattt    12060
tttaaatgtt catgtcacat cctaatagaa agaaattact tctagtcagt catccaggct    12120
tacctgcttg gtctagaatg gattttccc ggagccggaa gccaggagga aactacacca     12180
cactaaaaca ttgtctacag ctccagatgt ttctcatttt aaacaacttt ccactgacaa    12240
cgaaagtaaa gtaaagtatt ggattttttt aaagggaaca tgtgaatgaa tacacaggac    12300
ttattatatc agagtgagta atcggttggt tggttgattg attgattgat tgatacattc    12360
agcttcctgc tgctagcaat gccacgattt agatttaatg atgcttcagt ggaaatcaat    12420
cagaaggtat tctgaccttg tgaacatcag aaggtatttt ttaactccca agcagtagca    12480
ggacgatgat agggctggag ggctatggat tcccagccca tccctgtgaa ggagtaggcc    12540
```

```
actctttaag tgaaggattg gatgattgtt cataatacat aaagttctct gtaattacaa    12600
ctaaattatt atgccctctt ctcacagtca aaaggaactg ggtggtttgg ttttttgttgc    12660 ttttttagat ttattgtccc atgtgggatg agttttaaa tgccacaaga cataatttaa    12720
aataaataaa ctttgggaaa aggtgtaaga cagtagcccc atcacatttg tgatactgac    12780
aggtatcaac ccagaagccc atgaactgtg tttccatcct ttgcatttct ctgcgagtag    12840
ttccacacag gtttgtaagt aagtaagaaa gaaggcaaat tgattcaaat gttacaaaaa    12900
aacccttctt ggtggattag acaggttaaa tatataaaca aacaaacaaa aattgctcaa    12960 aaagaggag aaaagctcaa gaggaaaagc taaggactgg taggaaaaag ctttactctt    13020
tcatgccatt ttatttcttt ttgattttta aatcattcat tcaatagata ccaccgtgtg    13080
acctataatt ttgcaaatct gttacctctg acatcaagtg taattagctt ttggagagtg    13140
ggctgacatc aagtgtaatt agcttttgga gagtgggttt tgtccattat taataattaa    13200
ttaattaaca tcaaacacgg cttctcatgc tatttctacc tcactttggt tttggggtgt    13260
tcctgataat tgtgcacacc tgagttcaca gcttcaccac ttgtccattg cgttatttc    13320 ttttccttt ataattcttt cttttccctt cataattttc aaaagaaaac ccaaagctct    13380
aaggtaacaa attaccaaat tacatgaaga tttggttttt gtcttgcatt ttttttcctt    13440
atgtgacgct ggaccttttc tttacccaag gattttttaaa actcagattt aaaacaaggg    13500
gttactttac atcctactaa gaagtttaag taagtaagtt tcattctaaa atcagaggta    13560
aatagagtgc ataaataatt ttgttttaat cttttttgttt ttcttttaga cacattagct    13620
ctggagtgag tctgtcataa tatttgaaca aaaattgaga gctttattgc tgcattttaa    13680
gcataattaa tttggacatt atttcgtgtt gtgttcttta taaccaccga gtattaaact    13740
gtaaatcata atgtaactga agcataaaca tcacatggca tgttttgtca ttgttttcag    13800
gtactgagtt cttacttgag tatcataata tattgtgttt taacaccaac actgtaacat    13860
ttacgaatta ttttttaaa cttcagtttt actgcatttt cacaacatat cagacttcac    13920
caaatatatg ccttactatt gtattatagt actgctttac tgtgtatctc aataaagcac    13980
gcagttatgt tac                                                                  13993
```

<210> SEQ ID NO 2  
<211> LENGTH: 12436  
<212> TYPE: DNA  
<213> ORGANISM: Homo sapiens  
<300> PUBLICATION INFORMATION:  
<308> DATABASE ACCESSION NUMBER: NM_007124  
<309> DATABASE ENTRY DATE: 2010-08-04  
<313> RELEVANT RESIDUES IN SEQ ID NO: (1)..(12436)

<400> SEQUENCE: 2

```
gtattgatgt caagctgaac catcgtagga agttgaaagc cttagaaaga ggacttggta      60 aagttttgg attatcttga aactctggca agatggccaa gtatgagaa catgaagcca     120 gtcctgacaa tgggcagaac gaattcagtg atatcattaa gtccagatct gatgaacaca     180
atgacgtaca gaagaaaacc tttaccaaat ggataaatgc tcgattttca aagagtggga     240
aaccacccat caatgatatg ttcacagacc tcaaagatga aaggaagcta ttggatcttc     300
tagaaggcct cacaggaaca tcactgccaa aggaacgtgg ttccacaagg gtacatgcct     360
taaataacgt caacagagtg ctgcaggttt tacatcagaa caatgtggaa ttagtgaata     420 taggggggaac tgacattgtg gatggaaatc acaaactgac tttggggtta ctttggagca     480
```

-continued

```
tcattttgca ctggcaggtg aaagatgtca tgaaggatgt catgtcggac ctgcagcaga    540
cgaacagtga aagatcctg ctcagctggg tgcgtcagac caccaggccc tacagccaag     600
tcaacgtcct caacttcacc accagctgga cagatggact cgcctttaat gctgtcctcc    660
accgacataa acctgatctc ttcagctggg ataaagttgt caaaatgtca ccaattgaga    720
gacttgaaca tgccttcagc aaggctcaaa cttatttggg aattgaaaag ctgttagatc    780
ctgaagatgt tgccgttcag cttcctgaca agaaatccat aattatgtat ttaacatctt    840
tgtttgaggt gctacctcag caagtcacca tagacgccat ccgtgaggta gagacactcc    900
caaggaaata taaaaagaa tgtgaagaag aggcaattaa tatacagagt acagcgcctg     960
aggaggagca tgagagtccc cgagctgaaa ctcccagcac tgtcactgag gttgacatgg    1020
atctggacag ctatcagatt gcgttggagg aagtgctgac ctggttgctt tctgctgagg    1080
acactttcca ggagcaggat gatatttctg atgatgttga agaagtcaaa gaccagtttg    1140
caacccatga agcttttatg atggaactga ctgcacacca gagcagtgtg ggcagcgtcc    1200
tgcaggcagg caaccaactg ataacacaag gaactctgtc agacgaagaa gaatttgaga    1260
ttcaggaaca gatgaccctg ctgaatgcta gatgggaggc tcttagggtg gagagtatgg    1320
acagacagtc ccggctgcac gatgtgctga tggaactgca aagaagcaa ctgcagcagc     1380 tctccgcctg gttaacactc acagaggagc gcattcagaa gatggaaact gccccctgg    1440 atgatgatgt aaaatctcta caaaagctgc tagaagaaca taaagtttg caaagtgatc     1500 ttgaggctga acaggtgaaa gtaaattcac taactcacat ggtggtcatt gttgatgaaa    1560
acagtggtga gagtgctaca gctatcctag aagaccagtt acagaaactt ggtgagcgct    1620
ggacagcagt atgccgttgg actgaagaac gctggaatag gttacaagaa atcaatatat    1680
tgtggcagga attattggaa gaacagtgct tgttgaaagc ttggttaacc gaaaaagaag    1740
aggctttaaa taaagtccag acaagcaact tcaaagacca aaaggaacta agtgtcagtg    1800
ttcgacgtct ggctattttg aaggaagaca tggaaatgaa cgtcaaaca ttggatcagc     1860 tgagtgagat tggccaggat gtgggacaat tacttgataa ttccaaggca tctaagaaga    1920
tcaacagtga ctcagaggaa ctgactcaaa gatgggattc tttggttcag agactagaag    1980
attcctccaa ccaggtgact caggctgtag caaagctggg gatgtctcag attcctcaga    2040 aggaccttt ggagactgtt cgtgtaagag aacaagcaat tacaaaaaaa tctaagcagg     2100
aactgcctcc tcctcctccc ccaaagaaga gacagatcca tgtggatatt gaagctaaga    2160
aaaagtttga tgctataagt gcagagctgt tgaactggat tttgaaatgg aaaactgcca    2220
ttcagaccac agagataaaa gagtatatga agatgcaaga cacttccgaa atgaaaaaga    2280
agttgaaggc attagaaaaa gaacagagag aaagaatccc cagagcagat gaattaaacc    2340
aaactggaca aatccttgtg gagcaaatgg gaaaagaagg ccttcctact gaagaaataa    2400
aaaatgttct ggagaaggtt tcatcagaat ggaagaatgt atctcaacat ttggaagatc    2460
tagaaagaaa gattcagcta caggaagata taaatgctta tttcaagcag cttgatgagc    2520
ttgaaaaggt catcaagaca aaggaggagt gggtaaaaca cacttccatt tctgaatctt    2580
cccggcagtc cttgccaagc ttgaaggatt cctgtcagcg ggaattgaca aatcttcttg    2640
gccttcaccc caaaattgaa atggctcgtg caagctgctc ggccctgatg tctcagcctt    2700
ctgccccaga ttttgtccag cggggcttcg atagctttct gggccgctac caagctgtac    2760
aagaggctgt agaggatcgt caacaacatc tagagaatga actgaagggc caacctggac    2820
atgcatatct ggaaacattg aaaacactga agatgtgct aaatgattca gaaaataagg     2880
```

```
cccaggtgtc tctgaatgtc cttaatgatc ttgccaaggt ggagaaggcc ctgcaagaaa    2940
aaaagaccct tgatgaaatc cttgagaatc agaaacctgc attacataaa cttgcagaag    3000
aaacaaaggc tctggagaaa aatgttcatc ctgatgtaga aaattatat aagcaagaat     3060
ttgatgatgt gcaaggaaag tggaacaagc taaaggtctt ggtttccaaa gatctacatt    3120
tgcttgagga aattgctctc acactcagag cttttgaggc cgattcaaca gtcattgaga    3180
agtggatgga tggcgtgaaa gacttcttaa tgaaacagca ggctgcccaa ggagacgacg    3240
caggtctaca gaggcagtta gaccagtgct ctgcatttgt taatgaaata gaaacaattg    3300
aatcatctct gaaaaacatg aaggaaatag agactaatct tcgaagtggt ccagttgctg    3360
gaataaaaac ttgggtgcag acaagactag gtgactacca aactcaactg gagaaactta    3420
gcaaggagat cgctactcaa aaaagtaggt tgtctgaaag tcaagaaaaa gctgcgaacc    3480
tgaagaaaga cttggcagag atgcaggaat ggatgaccca ggccgaggaa gaatatttgg    3540
agcgggattt tgagtacaag tcaccagaag agcttgagag tgctgtggaa gagatgaaga    3600
gggcaaaaga ggatgtgttg cagaaggagg tgagagtgaa gattctcaag gacaacatca    3660
agttattagc tgccaaggtg ccctctggtg gccaggagtt gacgtctgag ctgaatgttg    3720
tgctggagaa ttaccaactt cttttgtaata gaattcgagg aaagtgccac acgctagagg    3780
aggtctggtc ttgttggatt gaactgcttc actatttgga tcttgaaact acctggttaa    3840
acactttgga agagcggatg aagagcacag aggtcctgcc tgagaagacg gatgctgtca    3900
acgaagccct ggagtctctg aatctgttc tgcgccaccc ggcagataat cgcacccaga    3960
ttcgagagct tggccagact ctgattgatg gggggatcct ggatgatata atcagtgaga    4020
aactggaggc tttcaacagc cgatatgaag atctaagtca cctggcagag agcaagcaga    4080
tttctttgga aaagcaactc caggtgctgc gggaaactga ccagatgctt caagtcttgc    4140
aagagagctt gggggagctg gacaaacagc tcaccacata cctgactgac aggatagatg    4200
cttttccaagt tccacaggaa gctcagaaaa tccaagcaga gatctcagcc catgagctaa    4260
ccctagagga gttgagaaga aatatgcgtt ctcagcccct gacctcccca gagagtagga    4320
ctgccagagg aggaagtcag atggatgtgc tacagaggaa actccgagag gtgtccacaa    4380
agttccagct tttccagaag ccagctaact tcgagcagcg catgctggac tgcaagcgtg    4440
tgctggatgg cgtgaaagca gaacttcacg ttctggatgt gaaggacgta gaccctgacg    4500
tcatacagac gcacctggac aagtgtatga aactgtataa aactttgagt gaagtcaaac    4560
ttgaagtgga aactgtgatt aaaacaggaa gacatattgt ccagaaacag caaacgagaa    4620
acccaaaagg gatggatgag cagctgactt ccctgaaggt tctttacaat gacctgggcg    4680
cacaggtgac agaaggaaaa caggatctgg aaagagcatc acagttggcc cggaaaatga    4740
agaaagaggc tgcttctctc tctgaatggc tttctgctac tgaaactgaa ttggtacaga    4800
agtccacttc agaaggtctg cttggtgact tggatacaga aatttcctgg gctaaaaatg    4860
ttctgaagga tctggaaaag agaaaagctg atttaaatac catcacagag agtagtgctg    4920
ccctgcaaaa cttgattgag ggcagtgagc ctatttaga agagaggctc tgcgtcctta    4980
acgctgggtg gagccgagtt cgtacctgga ctgaagattg gtgcaatacc ttgatgaacc    5040
atcagaacca gctagaaata tttgatggga acgtggctca cataagtacc tggctttatc    5100
aagctgaagc tctattggat gaaattgaaa agaaaccaac aagtaaacag gaagaaattg    5160
tgaagcgttt agtatctgag ctggatgatg ccaacctcca ggttgaaaat gtccgcgatc    5220
```

```
aagcccttat tttgatgaat gcccgtggaa gctcaagcag ggagcttgta gaaccaaagt    5280
tagctgagct gaataggaac tttgaaaagg tgtctcaaca tatcaaaagt gccaaattgc    5340
taattgctca ggaaccatta taccaatgtt tggtcaccac tgaaacattt gaaactggtg    5400
tgcctttctc tgacttggaa aaattagaaa atgacataga aaatatgtta aaatttgtgg    5460
aaaaacactt ggaatccagt gatgaagatg aaaagatgga tgaggagagt gcccagattg    5520
aggaagttct acaaagagga gaagaaatgt tacatcaacc tatggaagat aataaaaaag    5580
aaaagatccg tttgcaatta ttacttttgc atactagata caacaaaatt aaggcaatcc    5640
ctattcaaca gaggaaaatg ggtcaacttg cttctggaat tagatcatca cttcttccta    5700
cagattatct ggttgaaatt aacaaaattt tactttgcat ggatgatgtt gaattatcgc    5760
ttaatgttcc agagctcaac actgctattt acgaagactt ctcttttcag gaagactctc    5820
tgaagaatat caaagaccaa ctggacaaac ttggagagca gattgcagtc attcatgaaa    5880 acagccaga tgtcatcctt gaagcctctg gacctgaagc cattcagatc agagatacac    5940
ttactcagct gaatgcaaaa tgggacagaa ttaatagaat gtacagtgat cggaaaggtt    6000
gttttgacag ggcaatggaa gaatggagac agttccattg tgaccttaat gacctcacac    6060
agtggataac agaggctgaa gaattactgg ttgatacctg tgctccaggt ggcagcctgg    6120
acttagagaa agccaggata catcagcagg aacttgaggt gggcatcagc agccaccagc    6180
ccagttttgc agcactaaac cgaactgggg atggggattgt gcagaaactc tcccaggcag    6240
atggaagctt cttgaaagaa aaactggcag gtttaaacca acgctgggat gcaattgttg    6300
cagaagtgaa ggataggcag ccaaggctaa aggagaaag taagcaggtg atgaagtaca    6360
ggcatcagct agatgagatt atctgttggt taacaaaggc tgagcatgct atgcaaaaga    6420
gatcaaccac cgaattggga gaaaacctgc aagaattaag agacttaact caagaaatgg    6480
aagtacatgc tgaaaaactc aaatggctga atagaactga attggagatg ctttcagata    6540
aaagtctgag tttacctgaa agggataaaa tttcagaaag cttaaggact gtaaatatga    6600
catggaataa gatttgcaga gaggtgccta ccaccctgaa ggaatgcatc caggagccca    6660
gttctgtttc acagacaagg attgctgctc atcctaatgt ccaaaaggtg gtgctagtat    6720
catctgcgtc agatattcct gttcagtctc atcgtacttc ggaaatttca attcctgctg    6780
atcttgataa aactataaca gaactagccg actggctggt attaatcgac cagatgctga    6840
agtccaacat tgtcactgtt ggggatgtag aagagatcaa taagaccgtt tcccgaatga    6900
aaattacaaa ggctgactta aacagcgcc atcctcagct ggattatgtt tttacattgg    6960
cacagaattt gaaaaataaa gcttccagtt cagatatgag aacagcaatt acagaaaaat    7020
tggaaagggt caagaaccag tgggatggca cccagcatgg cgttgagcta agacagcagc    7080
agcttgagga catgattatt gacagtcttc agtgggatga ccatagggag gagactgaag    7140
aactgatgag aaaatatgag gctcgactct atattcttca gcaagcccga cgggatccac    7200
tcaccaaaca aatttctgat aaccaaatac tgcttcaaga actgggtcct ggagatggta    7260
tcgtcatggc gttcgataac gtcctgcaga aactcctgga ggaatatggg agtgatgaca    7320
caaggaatgt gaaagaaacc acagagtact aaaaacatc atggatcaat ctcaaacaaa    7380
gtattgctga cagacagaac gccttggagg ctgagtggag gacggtgcag gcctctcgca    7440
gagatctgga aaacttcctg aagtggatcc aagaagcaga gaccacagtg aatgtgcttg    7500
tggatgcctc tcatcgggag aatgctcttc aggatagtat cttggccagg gaactcaaac    7560
agcagatgca ggacatccag gcagaaattg atgcccacaa tgacatattt aaaagcattg    7620
```

```
acggaaacag gcagaagatg gtaaaagctt tgggaaattc tgaagaggct actatgcttc    7680
aacatcgact ggatgatatg aaccaaagat ggaatgactt aaaagcaaaa tctgctagca    7740
tcagggccca tttggaggcc agcgctgaga agtggaacag gttgctgatg tccttagaag    7800
aactgatcaa atggctgaat atgaaagatg aagagcttaa gaaacaaatg cctattggag    7860
gagatgttcc agccttacag ctccagtatg accattgtaa ggccctgaga cgggagttaa    7920
aggagaaaga atattctgtc ctgaatgctg tcgaccaggc ccgagttttc ttggctgatc    7980
agccaattga ggcccctgaa gagccaagaa gaaacctaca atcaaaaaca gaattaactc    8040
ctgaggagag agcccaaaag attgccaaag ccatgcgcaa acagtcttct gaagtcaaag    8100
aaaaatggga aagtctaaat gctgtaacta gcaattggca aaagcaagtg gacaaggcat    8160
tggagaaact cagagacctg cagggagcta tggatgacct ggacgctgac atgaaggagg    8220
cagagtccgt gcggaatggc tggaagcccg tgggagactt actcattgac tcgctgcagg    8280
atcacattga aaaaatcatg gcatttagag aagaaattgc accaatcaac tttaaagtta    8340
aaacggtgaa tgatttatcc agtcagctgt ctccacttga cctgcatccc tctctaaaga    8400
tgtctcgcca gctagatgac cttaatatgc gatggaaact tttacaggtt tctgtggatg    8460
atcgccttaa acagcttcag gaagcccaca gagattttgg accatcctct cagcattttc    8520
tctctacgtc agtccagctg ccgtggcaaa gatccatttc acataataaa gtgccctatt    8580
acatcaacca tcaaacacag accacctgtt gggaccatcc taaaatgacc gaactctttc    8640
aatcccttgc tgacctgaat aatgtacgtt tttctgccta ccgtacagca atcaaaatcc    8700
gaagactaca aaaagcacta tgtttggatc tcttagagtt gagtacaaca aatgaaattt    8760
tcaaacagca caagttgaac caaaatgacc agctcctcag tgttccagat gtcatcaact    8820
gtctgacaac aacttatgat ggacttgagc aaatgcataa ggacctggtc aacgttccac    8880
tctgtgttga tatgtgtctc aattggttgc tcaatgtcta tgacacgggt cgaactggaa    8940
aaattagagt gcagagtctg aagattggat taatgtctct ctccaaaggt ctcttggaag    9000
aaaaatacag atatctcttt aaggaagttg cagggccaac agaaatgtgt gaccagaggc    9060
agctgggcct gttacttcat gatgccatcc agatcccccg gcagctaggt gaagtagcag    9120
cttttggagg cagtaatatt gagcctagtg ttcgcagctg cttccaacag aataacaata    9180
aaccagaaat aagtgtgaaa gagtttatag attggatgca tttggaacca cagtccatgg    9240
tttggctccc agttttacat cgagtggcag cagcggagac tgcaaaacat caggccaaat    9300
gcaacatctg taaagaatgt ccaattgtcg ggttcaggta tagaagcctt aagcatttta    9360
actatgatgt ctgccagagt tgtttctttt cgggtcgaac agcaaaaggt cacaaattac    9420
attacccaat ggtggaatat tgtataccta aacatctgg ggaagatgta cgagacttca    9480
caaaggtact taagaacaag ttcaggtcga agaagtactt tgccaaacac cctcgacttg    9540
gttacctgcc tgtccagaca gttcttgaag gtgacaactt agagactcct atcacactca    9600
tcagtatgtg gccagagcac tatgaccct cacaatctcc tcaactgttt catgatgaca    9660
cccattcaag aatagaacaa tatgccacac gactggccca gatggaaagg actaatgggt    9720
cttttctcac tgatagcagc tccaccacag gaagtgtgga agacgagcac gccctcatcc    9780
agcagtattg ccaaacactc ggaggagagt ccccagtgag ccagccgcag agcccagctc    9840
agatcctgaa gtcagtagag agggaagaac gtggagaact ggagaggatc attgctgacc    9900
tggaggaaga acaaagaaat ctacaggtgg agtatgagca gctgaaggac cagcacctcc    9960
```

```
gaaggggggct ccctgtcggt tcaccgccag agtcgattat atctccccat cacacgtctg   10020
aggattcaga acttatagca gaagcaaaac tcctcaggca gcacaaaggt cggctggagg   10080
ctaggatgca gattttagaa gatcacaata aacagctgga gtctcagctc caccgcctcc   10140
gacagctgct ggagcagcct gaatctgatt cccgaatcaa tggtgtttcc ccatgggctt   10200
ctcctcagca ttctgcactg agctactcgc ttgatccaga tgcctccggc ccacagttcc   10260
accaggcagc gggagaggac ctgctggccc caccgcacga caccagcacg gatctcacgg   10320
aggtcatgga gcagattcac agcacgtttc catcttgctg cccaaatgtt cccagcaggc   10380
cacaggcaat gtgaagtatt catccggcca accaatgttt cctgacgtac agtgttgccc   10440
ttttcagcaa atgccaattc caagttccat aaatcagaa gctccatggc tccttggccc    10500
acgatgttga gtgctgactg tgtgttctac tgaaagagta aaacactgac tatccaaaga   10560
gaaatggata ttttgttttt ataataacca tatattattg ttttcttctt ccctttctat   10620
gcaagtgtaa attaatgaac agagaggtat ttggaaatgg taatacattt gtcacggatt   10680
tgtataatgt atacagcatt gggaaagtgg gtggggcctt tctaatatga taccgtcttt   10740
ttaataacta tgacaaagct tacataagaa ttagaagacc actttacatt tttacattcc   10800
ttctgctgtt catattaacc ttgcacaatt acttcatttt ttctttgact cttttaccac   10860
aatgttttgg ttatttataa tttatcagcc atatgtttat cagccatata accaactaga   10920
tcccaaatag atccatgtat ttgtttccgt gatttggcca cattaataaa ttcataaatt   10980
tcaatcaaat atcttatata tacacacata tggtttaagc tacagccctg tgtatgccgt   11040
ttaactttat ttgacgttgc ccacttactt ctttgctgac cacttggata accgtaataa   11100
aaatcctata agcctaaatg gcatttcttt tgggatattt ttcctgcatt ttattcccectt  11160 tttatataag taggaattaa ttatttattt tatgtcttaa tctatttgat aaagaagact   11220
acattataat aatctcaaag atcatattac caaaggttgc ccacttgagc atatttcat    11280 tttgacacag aaacaaaatt tagtacaacc tttcctagtt cccatgtctt gattttcatc   11340
attacatgca cagcagacct ttacctattg tgataccaga acacatcatt gtctttggtt   11400
cccttcaaag agaattttat tgttgttttg tattttcaag tccttaatag ttcttgaaac   11460
tcctagttgt tttcttgttg aaagcagaca cacatttagt gcacggctta ttttacctttt  11520 cgggtgaaaa atcagatgtt tttataccct tcacttgatc aatatatttg gaagaatgt    11580 ttatcaaaag tctatgtcac tgcttctaca gaagaatgaa attaatgctt aggtgatggt   11640
acctccacct acatcttttt gagtgcattc aattatgtat tttggtttag cttctgattt   11700
aacatttaat tgattcagtt taaacatgtt acttaattag caaatgtaga ggaaccaaaa   11760
aaaggtgaaa ataatatgtt ttgattcaaa cctaaagaca taaaaacata aagcattttt   11820
aactttgggt tctctttagc tgggatctgg ccagaaggag gcttaaagtt agaaattgct   11880
attattttag aataggttgg gtgggttggg gggcaagggt gtctatttgc agcagagata   11940
ttttgaaaag aagaaaattg ttttatataa aaaggaaagc catgaccacc tttctacctc   12000
agatccatct tcatccattg cattggaaac tgctttatgc tgctgcagtc tgcaaagtct   12060
agagctttta tcaggccatg tcatacccaa gaaagcacct atttaaagaa aaacaattc    12120 cctgagctct caactccaag ttgtagattt ggtgtcttcc ttgttcttac tttaaaaagt   12180
catgtgttaa ttttttttcct gcctgtattt gtatgcaaaa tgtcctctat ctgctattaa   12240
agaaaagcta cgtaaaacac tacattgtaa ccttctaagt aataataaat aaaaagaaat   12300
atattgcagt aacaatggga agtaagtatg tagttctttt gaaatatgtg gtaaagaact   12360
```

| | |
|---|---:|
| aatcacagac tatcatctaa tctggttaca tattgtattt ttcatcctga ataaaagtaa | 12420 |
| ttttaacaca aaaaaa | 12436 |

<210> SEQ ID NO 3
<211> LENGTH: 378
<212> TYPE: DNA
<213> ORGANISM: Homo sapiens

<400> SEQUENCE: 3

| | |
|---|---:|
| aggttagaga atcgcttgaa ccagggagga ggaggtcgca gcaagctgag atcgggccac | 60 |
| tgcactccac cctgggtgag agagtgagac tccatctcaa aaaacaaaca aacaaaaaat | 120 |
| taaaaagaa aaaacagtg gctcaaaatg cataatgctt gcctagagca taacagggaa | 180 |
| aaaaggaaaa tcagatgctt ttagaagact gatacactga aaactatttg agcgttctgt | 240 |
| taatcaataa atcctaaacc taccaataca aatggaactt atcatgcagc caatccagta | 300 |
| aataatggta gctggaagta atgatagtga ttgtaaaaac tatggctggg catggtggct | 360 |
| catgcctgta atccgagc | 378 |

<210> SEQ ID NO 4
<211> LENGTH: 294
<212> TYPE: DNA
<213> ORGANISM: Homo sapiens

<400> SEQUENCE: 4

| | |
|---|---:|
| ctcaggttct ctgcctgcac atctctttca tctggctcct ttacatgtca gatgaaagaa | 60 |
| ttatctcacc attccggctc aacaagaaat tcagtcccga acagacaaaa aagtttaaaa | 120 |
| atattttata aacattaacc tggacttttc gtagaagaaa taaagctgag aacgtcatat | 180 |
| ttcagcagct tcaatacttg ttttctgatt gaatcataaa ttttattact ttatacttgc | 240 |
| ttctacaatg acaaagtacc caaagctaaa tgtgaatctc tagtaggtcg aaa | 294 |

<210> SEQ ID NO 5
<211> LENGTH: 686
<212> TYPE: DNA
<213> ORGANISM: Homo sapiens

<400> SEQUENCE: 5

| | |
|---|---:|
| cgtcgaagct catcaaaaat attgattgaa tgacagttaa agagccttta ctgtattta | 60 |
| atttccaata acatatatg tgtcacatat ttttaaaaat atggagaagt tcagcgtttt | 120 |
| tgttttgctt tactttggta ggttaatgcc tgatgttcat cttttccagt tcaacaggct | 180 |
| gggtgagtgg tatggtacca taaaaggat gatcagctgg aaatcaagac cttcaatctc | 240 |
| tacttccatt ccctctaaca aacagccatg gcatgttgtc atttaattct gagagagctt | 300 |
| catttccaca tcttcagaaa gacagaacaa tgctagatgt acttgcatgt attccaatag | 360 |
| tgattgcctt tcagaccttc ctcttctccc atttgaatag acattagcct catgagtgac | 420 |
| ctccgcacct gtactctccc catacacgat tctgcatata gccaccaaat gtaactttct | 480 |
| aatatgcaaa acataaaaaa aaacttcctg gttttttga acacattcat ctcaattgag | 540 |
| caaggaatca tccatccaca ttgtatcccc agtccaccctt tcccgcatcc tttttcaattt | 600 |
| tttgccaatt gcccatatcc caaaacctcc aatgagcttg ggaagtgggg tacgactcga | 660 |
| attcgtatct ggcatagtgt tctgga | 686 |

<210> SEQ ID NO 6

```
<211> LENGTH: 480
<212> TYPE: DNA
<213> ORGANISM: Homo sapiens

<400> SEQUENCE: 6
ctcaacgctt tatactcaca tccaattata cttcgcatcc aattatactt catatacaaa      60
gtataagctc tccagtttgc tgtagtcctc atcactccct atccttttt atacgcaact     120
catctcactt ccttatgtta tgtttctggc ttctacaata ggcatttgga tttggtgccc     180
cccgggtct tgatcacagc ttctcaaact taaatatgga tacagcccac ctggtgattc      240
tgatttaaat tcacggggtt gggtcgaaga attcagttct aaccagcttc caggtgaaac     300
caatgttgct gggtcatgga tcacactttg aatgacaacg ttccaggtaa gaatattatt     360
tatttgaaaa ccactgctag tctacttaag gtatgtgttc gatctattag ttactactgc     420
tgaaactcag aagatataga tttatgtgac actggcaggg aagtataaag cgttgagggg     480

<210> SEQ ID NO 7
<211> LENGTH: 501
<212> TYPE: DNA
<213> ORGANISM: Homo sapiens

<400> SEQUENCE: 7
gcccatcaat gggagaaggt ctgttatggg aagactgtat tgaattaaaa ggttaatatc      60
aggctgagct cagtggctca tacctgtaat cccagcactt tgggaggttg atgctattac     120
tatctctact ttactcaggc acagagcagc taagccattt gtccaggttc acagagctag     180
caggtggcca tgcttacacc cacagcacct gatactgtct gaaccattcc ctaaagtatt     240
tctacagaag agtactaata agattttta atcctgcagg attttcta ttattctttt       300
caaatattgt gtaatctaat accatgccat ccttgatatc taactcattt tagagataaa     360
aatgcttacc ctaaatacca tcatataatc tatatttcta taaccccaac agcaatattg     420
caggttagaa tccaagtgtg cagaatattt gtgaagatca gtgtagataa tactgaaatg     480
acagtgatga ggaagaaggt a                                               501

<210> SEQ ID NO 8
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 8
ucucacucuc ucacccaggg uggagug                                          27

<210> SEQ ID NO 9
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 9
agcugcugaa auaugacguu cucagcu                                          27

<210> SEQ ID NO 10
<211> LENGTH: 27
<212> TYPE: DNA
<213> ORGANISM: Artificial Sequence
<220> FEATURE:
<223> OTHER INFORMATION: Antisense oligonucleotide
```

```
-continued

<400> SEQUENCE: 10
aggcauuaac cuaccaaagu aaagcaa                                              27

<210> SEQ ID NO 11
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 11
gaaaguuaca uuggguggcu auaugca                                              27

<210> SEQ ID NO 12
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 12
uacagcaaac uggagagcuu auacuuu                                              27

<210> SEQ ID NO 13
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 13
uuccauuugu auugguaggu uuaggau                                              27

<210> SEQ ID NO 14
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 14
cggaauggug agauaauucu uucaucu                                              27

<210> SEQ ID NO 15
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 15
cgugaauuua aaucagaauc accaggu                                              27

<210> SEQ ID NO 16
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 16
guaacuaaua gaucgaacac auaccuu                                              27

<210> SEQ ID NO 17
```

-continued

```
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 17
agggaaugga aguagagauu gaagguc                                          27

<210> SEQ ID NO 18
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 18
gccacctgct agctctgtga                                                  20

<210> SEQ ID NO 19
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 19
taccttcttc ctcatcact                                                   19

<210> SEQ ID NO 20
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 20
gggattacag gtatgagcca c                                                21

<210> SEQ ID NO 21
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 21
ggttcagaca gtatcaggtg c                                                21

<210> SEQ ID NO 22
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 22
tcccataaca gaccttctcc c                                                21

<210> SEQ ID NO 23
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 8
```

```
<400> SEQUENCE: 23
cuccacccug ggugagagag ugaga                                          25

<210> SEQ ID NO 24
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 9

<400> SEQUENCE: 24
cugagaacgu cauauuucag cagct                                          25

<210> SEQ ID NO 25
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 10

<400> SEQUENCE: 25
gcuuuacuuu gguagguuaa ugcct                                          25

<210> SEQ ID NO 26
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 11

<400> SEQUENCE: 26
cauauagcca ccaaauguaa cuutc                                          25

<210> SEQ ID NO 27
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 12

<400> SEQUENCE: 27
aguauaagcu cuccaguuug cugta                                          25

<210> SEQ ID NO 28
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 13

<400> SEQUENCE: 28
ccuaaaccua ccaauacaaa uggaa                                          25

<210> SEQ ID NO 29
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 14

<400> SEQUENCE: 29
```

```
augaaagaau uaucucacca uuccg                                              25

<210> SEQ ID NO 30
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 15

<400> SEQUENCE: 30
cuggugauuc ugauuuaaau ucacg                                              25

<210> SEQ ID NO 31
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 16

<400> SEQUENCE: 31
gguauguguu cgaucuauua guuac                                              25

<210> SEQ ID NO 32
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 17

<400> SEQUENCE: 32
ccuucaaucu cuacuuccau uccct                                              25
```